US011490985B2

(12) United States Patent
Ueda

(10) Patent No.: US 11,490,985 B2
(45) Date of Patent: Nov. 8, 2022

(54) MEDICAL OBSERVATION APPARATUS AND CONTROL METHOD

(71) Applicant: Sony Olympus Medical Solutions Inc., Tokyo (JP)

(72) Inventor: Masaaki Ueda, Kanagawa (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 288 days.

(21) Appl. No.: 16/492,944

(22) PCT Filed: Jan. 12, 2018

(86) PCT No.: PCT/JP2018/000696
§ 371 (c)(1),
(2) Date: Sep. 11, 2019

(87) PCT Pub. No.: WO2018/179675
PCT Pub. Date: Oct. 4, 2018

(65) Prior Publication Data
US 2020/0015928 A1 Jan. 16, 2020

(30) Foreign Application Priority Data
Mar. 29, 2017 (JP) .............................. JP2017-064200

(51) Int. Cl.
G06K 9/00 (2022.01)
A61B 90/00 (2016.01)
(Continued)

(52) U.S. Cl.
CPC .............. A61B 90/37 (2016.02); A61B 90/25 (2016.02); G06T 1/0014 (2013.01)

(58) Field of Classification Search
CPC .................... A61B 90/37; A61B 90/25; A61B 2017/00973; A61B 2034/2065;
(Continued)

(56) References Cited

U.S. PATENT DOCUMENTS 11,256,963 B2 * 2/2022 Katayama ............... G06V 10/56
2001/0055062 A1 * 12/2001 Shioda ................... G02B 21/22
348/79

(Continued)

FOREIGN PATENT DOCUMENTS

JP 2001-112774 A 4/2001
JP 2002-336269 A 11/2002

(Continued)

OTHER PUBLICATIONS

European Search Report dated Jan. 2, 2020 in European Patent Application No. 18777771.9, 7 pages.
(Continued)

Primary Examiner — Avinash Yentrapati
(74) Attorney, Agent, or Firm — Xsensus, LLP

(57) ABSTRACT

There is provided a medical observation apparatus including: a determination unit which determines an apparatus to be used based on a captured image for medical use captured by an imaging device; and a display control unit which causes a related image for medical use corresponding to the determined apparatus and the captured image for medical use to be displayed.

21 Claims, 14 Drawing Sheets

(51) Int. Cl.
*A61B 90/25* (2016.01)
*G06T 1/00* (2006.01)

(58) Field of Classification Search
CPC ...... A61B 2034/2068; A61B 2034/254; A61B 2034/256; A61B 2090/365; A61B 2576/00; A61B 34/20; A61B 34/25; A61B 90/20; A61B 90/361; A61B 34/00; G06T 1/0014; G16H 30/40
See application file for complete search history.

(56) References Cited

U.S. PATENT DOCUMENTS

| | | | | |
|---|---|---|---|---|
| 2004/0070822 | A1* | 4/2004 | Shioda | A61B 90/25 |
| | | | | 359/372 |
| 2005/0145257 | A1* | 7/2005 | Barrera | A61B 34/20 |
| | | | | 128/898 |
| 2006/0293557 | A1* | 12/2006 | Chuanggui | A61B 34/20 |
| | | | | 600/101 |
| 2016/0000517 | A1* | 1/2016 | Kehat | A61B 34/25 |
| | | | | 600/103 |
| 2016/0287337 | A1* | 10/2016 | Aram | A61B 34/10 |
| 2017/0105809 | A1* | 4/2017 | Kruger | A61B 90/37 |

FOREIGN PATENT DOCUMENTS

| | | | |
|---|---|---|---|
| JP | 2002336269 A | * 11/2002 | ............ A61B 90/37 |
| JP | 2003-111773 A | 4/2003 | |
| JP | 2004-016357 | 1/2004 | |
| JP | 2017-038285 A | 2/2017 | |
| WO | 2016/149345 A1 | 9/2016 | |

OTHER PUBLICATIONS

International Search Report and Written Opinion dated Feb. 13, 2018 for PCT/JP2018/000696 filed on Jan. 12, 2018, 7 pages including English Translation of the International Search Report.

* cited by examiner

FIG.6
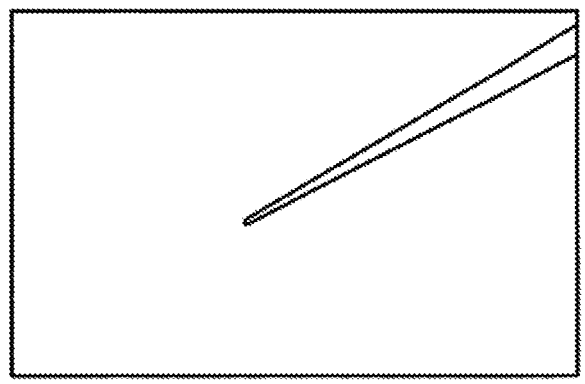
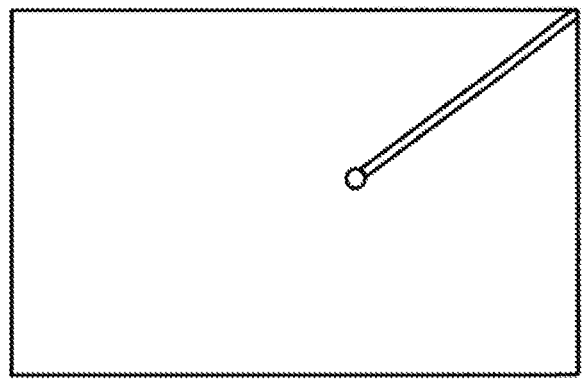
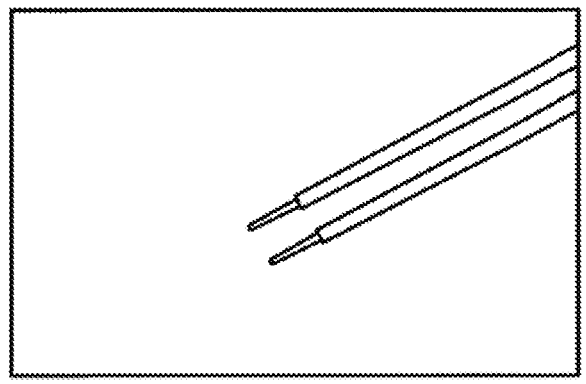

FIG.8
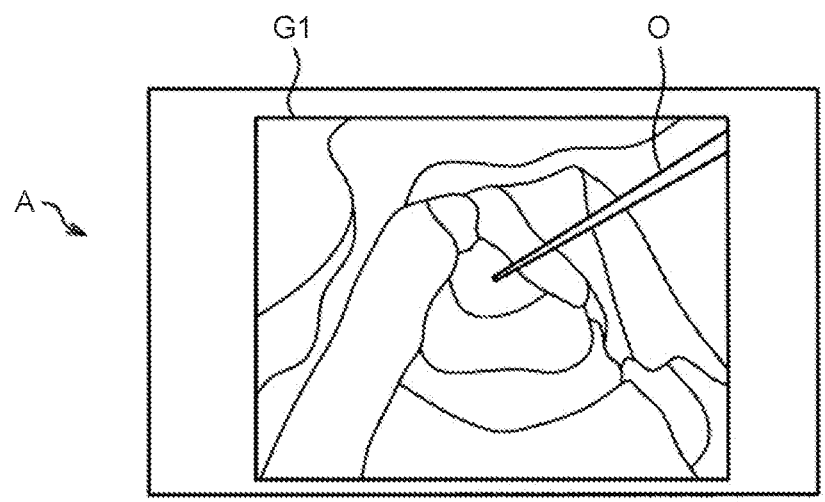
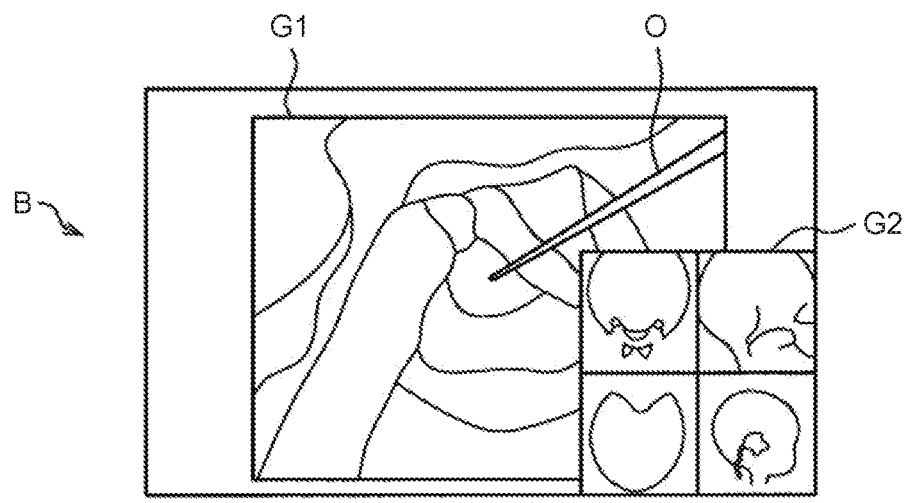

MEDICAL OBSERVATION APPARATUS AND CONTROL METHOD

CROSS-REFERENCE TO RELATED APPLICATIONS

The present application is based on PCT filing PCT/JP2018/000696, filed Jan. 12, 2018, which claims priority to JP 2017-064200, filed Mar. 29, 2017, the entire contents of each are incorporated herein by reference.

TECHNICAL FIELD

The present disclosure relates to a medical observation apparatus and a control method.

BACKGROUND ART

In recent years, in a medical field, a medical observation apparatus capable of magnifying and observing an observation target such as an affected site may be used to support surgery. Examples of the medical observation apparatus include a medical observation apparatus equipped with an optical microscope and a medical observation apparatus equipped with an imaging device functioning as an electronic imaging type microscope. Hereinafter, the medical observation apparatus equipped with the optical microscope is referred to as "optical medical observation apparatus". In addition, hereinafter, the medical observation apparatus equipped with the imaging device may refer to as an "electronic imaging type medical observation apparatus" or only a "medical observation apparatus".

In addition, technologies related to a surgical system have been developed to easily set a treatment apparatus such as an ultrasonic aspirator. Examples of the technologies may include the technology described in the following Patent Literature 1.

CITATION LIST

Patent Literature

Patent Literature 1: Japanese Laid-open Patent Publication No. 2003-111773

DISCLOSURE OF INVENTION

Technical Problem

For example, in micro surgery such as neurosurgical surgery, "various medical imaging apparatuses (modality apparatus) such as a navigation apparatus, an endoscope, and a nerve monitor" or "various treatment apparatuses such as an electrocautery, a bipolar, or an ultrasonic aspirator" are used in addition to medical observation apparatuses such as an optical medical observation apparatus or an electronic imaging type medical observation apparatus. Hereinafter, apparatuses related to medical practices, such as a medical imaging apparatus or a treatment apparatus, may be collectively referred to as "medical apparatus".

The medical apparatuses such as the medical imaging apparatus and the treatment apparatus described above may need to be set individually according to the progress of surgery, and images obtained from the medical imaging apparatus may need to be switched according to the progress of surgery. Therefore, medical workers such as an operator and a nurse need to always pay attention to the setting of the medical apparatuses and the like, and need to set the medical apparatuses appropriately.

Here, in the technology described in Patent Literature 1, conditions for an energy treatment tool such as the ultrasonic aspirator is set based on a comparison result of a diagnostic image acquired by a light scanning probe with images of a plurality of treatment sites stored in the diagnostic image database. Therefore, when the technology described in Patent Literature 1 is used, the conditions for the energy treatment tool are automatically set, so there is a possibility that the processing apparatuses such as the ultrasonic aspirator can be easily set.

However, in the technology described in Patent Literature 1, the conditions for the energy treatment tool are set based on the images of the treatment site stored in the diagnostic image database. Therefore, there is no guarantee that the conditions for patients who are subjected to medical practice are not always set optimally. In addition, in the technology described in Patent Literature 1, although it is possible to change the setting state of the energy treatment tool to a desired state, when a change operation may be required after the conditions of the energy treatment tool are automatically set, there is a possibility that the progress of medical practices such as surgery may be impeded.

The present disclosure is to provide a new and improved medical observation apparatus capable of supporting medical workers and a control method.

Solution to Problem

According to the present disclosure, there is provided a medical observation apparatus including: a determination unit configured to determine an apparatus to be used based on a captured image for medical use captured by an imaging device; and a display control unit configured to cause a related image for medical use corresponding to the determined apparatus and the captured image for medical use to be displayed.

According to the present disclosure, there is provided a control method executed by a medical observation apparatus, the method including: a step of determining an apparatus to be used based on a captured image for medical use captured by an imaging device; and a step of displaying a related image for medical use corresponding to the determined apparatus and the captured image for medical use.

Advantageous Effects of Invention

According to the present disclosure, it is possible to support medical workers.

It is to be noted that the above effects are not necessarily limited, and, along with or instead of the above effects, any of the effects described in the present specification or other effects which can be understood from the present specification may be exhibited.

BRIEF DESCRIPTION OF DRAWINGS

FIG. 6 is an explanatory view illustrating an example of apparatus determination information corresponding to an instrument used in the apparatus to be determined illustrated in FIG. 5.

FIG. 8 is an explanatory view illustrating an example of an image displayed on a display screen of a display apparatus in the first example of the use case realized by the processing related to the control method according to the present embodiment.

BEST MODE FOR CARRYING OUT THE INVENTION

Figure 1:
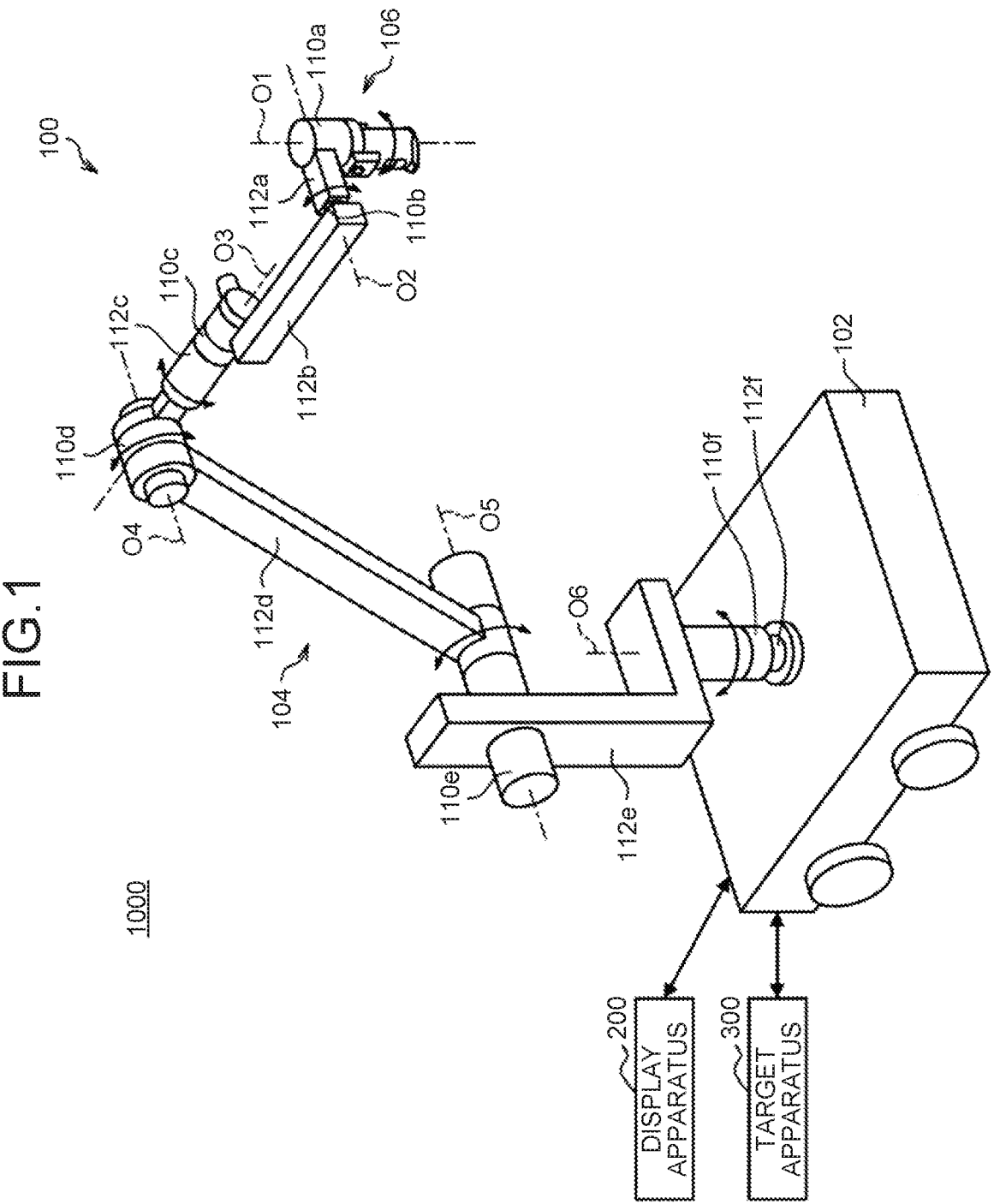
FIG. 1 is an explanatory view illustrating an example of a configuration of a medical observation system according to the present embodiment.

Hereinafter, preferred embodiments of the present disclosure will be described in detail with reference to the accompanying drawings. In the present specification and the drawings, components having substantially the same functional configuration will be denoted by the same reference numerals and a redundant description thereof will be omitted.

In addition, hereinafter, the present disclosure will be described in the following order.

1. Medical observation system according to the present embodiment and control method according to the present embodiment 2. Program according to the present embodiment ((Medical Observation System According to Present Embodiment and Control Method according to Present Embodiment)

Hereinafter, an example of a control method according to the present embodiment will be described while describing an example of a medical observation system according to the present embodiment.

[1] Configuration of Medical Observation System

FIG. 1 is an explanatory view illustrating an example of a configuration of a medical observation system 1000 according to the present embodiment. The medical observation system 1000 includes, for example, a medical observation apparatus 100, a display apparatus 200, and a target apparatus 300. The target apparatus 300 is an apparatus to be processed by a control method according to the present embodiment which is executed by the medical observation apparatus 100.

In addition, the medical observation system according to the present embodiment is not limited to an example illustrated in FIG. 1.

For example, the medical observation system according to the present embodiment may further include a control apparatus (not illustrated) which controls various operations executed by the medical observation apparatus 100. In the medical observation system 1000 illustrated in FIG. 1, as described below, an example in which the medical observation apparatus 100 includes a control unit (described below) which performs processing related to a control method according to the present embodiment, and thus the medical observation apparatus 100 includes a function of the control apparatus (not illustrated) is illustrated.

As the control apparatus (not illustrated), for example, arbitrary equipment which can perform the processing related to the control method according to the present embodiment, such as a "medical controller" or a "computer such as a server" may be used. In addition, the control apparatus (not illustrated) may be, for example, an integrated circuit (IC) which can be incorporated into the equipment as described above.

In addition, the medical observation system according to the present embodiment may have a configuration in which a plurality of medical observation apparatuses 100 and display apparatuses 200 are provided. When the plurality of medical observation apparatuses 100 are provided, in each of the medical observation apparatuses 100, the processing related to a control method of the medical observation apparatus 100 described below is performed. In addition, when the medical observation system according to the present embodiment is configured to include the plurality of medical observation apparatuses 100 and display apparatuses 200, the medical observation apparatus 100 and the display apparatus 200 may correspond to each other one-to-one and the plurality of medical observation apparatuses 100 may be associated with one display apparatus 200. When the plurality of medical observation apparatuses 100 are associated with one display apparatus 200, the display apparatus 200 performs, for example, a switching operation to display an image captured by any one of the medical observation apparatuses 100 on a display screen.

In addition, the medical observation system according to the present embodiment may be configured to include a plurality of target apparatuses 300. When the plurality of target apparatuses 300 are provided, the medical observation apparatus 100 sets each of the plurality of target apparatuses 300 as a target to be processed by the control method according to the present embodiment.

Figure 2:
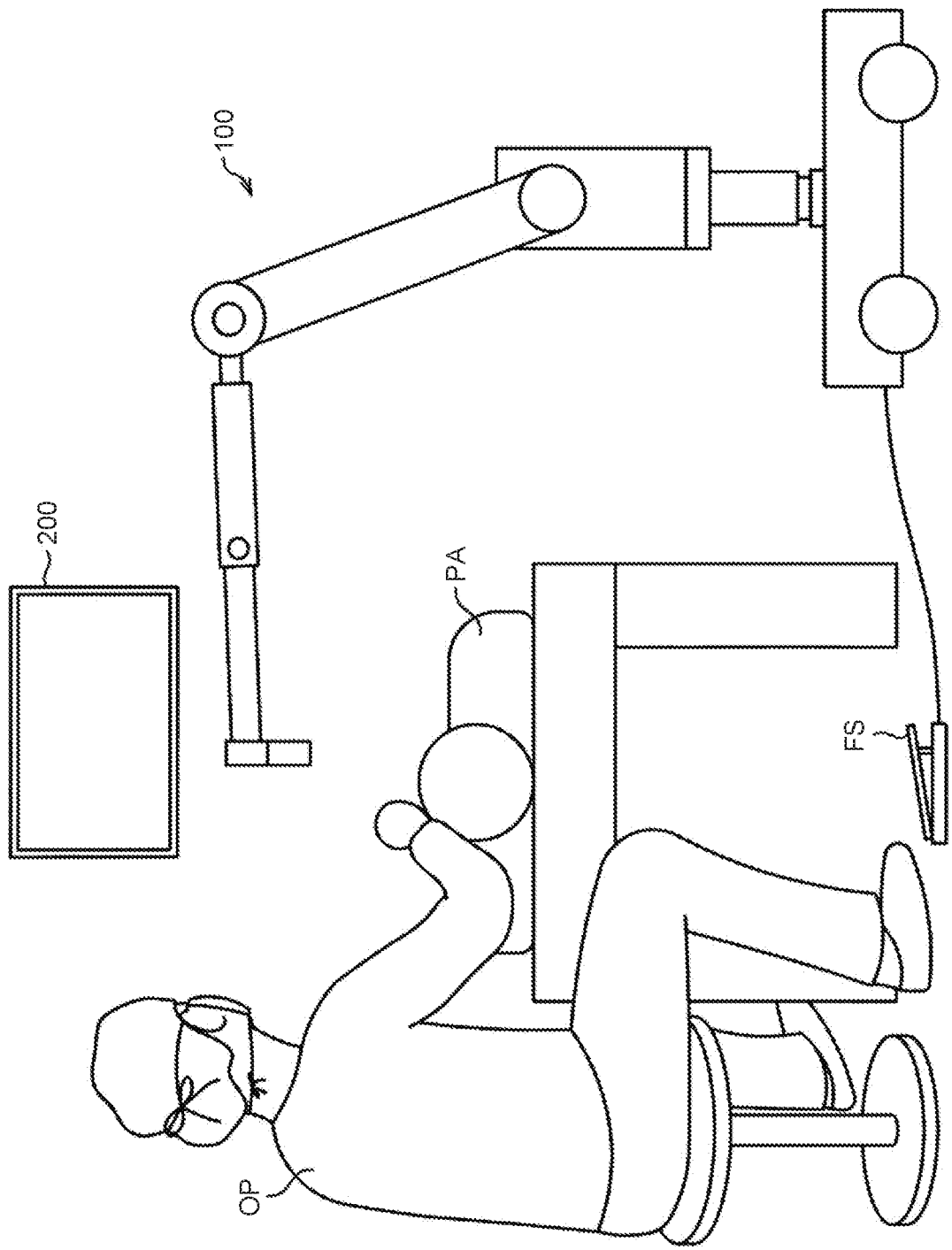
FIG. 2 is an explanatory view illustrating an example of a case where the medical observation system according to the present embodiment is used.

FIG. 2 is an explanatory view illustrating an example of a case where the medical observation system 1000 according to the present embodiment is used.

A patient PA to be observed (a patient to be subjected to a medical practice) is captured by an imaging device (described below) included in the medical observation apparatus 100. Hereinafter, the image captured by the medical observation apparatus according to the present embodiment, such as a captured image obtained by capturing a patient who is subjected to the above-described medical practice is referred to as a "captured image for medical use".

The captured image for medical use captured by the medical observation apparatus 100 is displayed on the display screen of the display apparatus 200. An operator OP (an example of a user of the medical observation apparatus 100) who performs a medical practice using the medical observation apparatus 100 performs a medical practice on a patient PA while looking at the captured image for medical use displayed on the display screen of the display apparatus 200.

In addition, the operator OP operates an external operation device of the medical observation apparatus 100 such as a foot switch FS or an operation device (described below) included in the medical observation apparatus 100 to operate an arm (described below), an imaging device (described below) or the like included in the medical observation apparatus 100, thereby making the medical observation apparatus 100 into a desired state.

Hereinafter, each apparatus which configures the medical observation system 1000 will be described.

[1-1] Display Apparatus 200

The display apparatus 200 is display means in the medical observation system 1000, and corresponds to an external display device as viewed from the medical observation apparatus 100. The display apparatus 200 displays, for example, various images such as an image (a moving image or a plurality of still images. The same will apply below) captured by the medical observation apparatus 100 or an image related to a user interface (UI) on the display screen. In addition, the display apparatus 200 may be configured to be capable of 3D display. The display by the display apparatus 200 is controlled by, for example, the medical observation apparatus 100 or the control apparatus (not illustrated).

In the medical observation system 1000, the display apparatus 200 is installed, for example, at any locations such as a wall, a ceiling, or a floor of an operating room which persons involved in an operation, such as an operator, are visually recognized in an operating room. Examples of the display apparatus 200 include, for example, a liquid crystal display, an organic electro-luminescence (EL) display, a cathode ray tube (CRT) display or the like.

The display apparatus 200 is not limited to the above example.

For example, the display apparatus 200 may be any wearable apparatuses, such as a head mounted display or an eyewear type apparatus, which are worn on a body of an operator or the like.

The display apparatus 200 is driven by, for example, power supplied from an internal power supply such as a battery included in the display apparatus 200, power supplied from the connected external power supply, or the like.

[1-2] Target Apparatus 300

The target apparatus 300 is an apparatus to be processed by a control method according to the present embodiment in the medical observation apparatus 100. As will be described below, the target apparatus 300 is a determination target that determines a use in the medical observation apparatus 100. In addition, as will be described below, in the medical observation apparatus 100, the target apparatus 300 can be a control target to be further controlled.

The target apparatus 300 may be any medical apparatuses such as "various medical imaging apparatuses such as a navigation apparatus, an endoscope, and a nerve monitor", and various treatment apparatuses such as an electrocautery, a bipolar, and an ultrasonic aspirator.

The target apparatus 300 is driven by, for example, power supplied from an internal power supply such as a battery included in the target apparatus 300, power supplied from the connected external power supply, or the like.

[1-3] Medical Observation Apparatus 100

The medical observation apparatus 100 is an electronic imaging type medical observation apparatus. For example, when the medical observation apparatus 100 is used during surgery, an operator (an example of a user of the medical observation apparatus 100) observes an operation site while referring to the captured image for medical use which is captured by the medical observation apparatus 100 and displayed on the display screen of the display apparatus 200, and performs various treatments, such as procedures according to the operation method, on the operation site.

First, an example of a hardware configuration of the medical observation apparatus 100 will be described with reference to FIG. 1.

The medical observation apparatus 100 includes, for example, a base 102, an arm 104, and an imaging device 106.

Although not illustrated in FIG. 1, the medical observation apparatus 100 may include, for example, one or more processors (not illustrated) which are constituted by arithmetic circuits such as a micro processing unit (MPU), a read only memory (ROM (not illustrated)), a random access memory (RAM (not illustrated)), a recording medium (not illustrated), and a communication device (not illustrated). The medical observation apparatus 100 is driven by, for example, power supplied from an internal power supply such as a battery included in the medical observation apparatus 100, power supplied from the connected external power supply or the like.

The processor (not illustrated) functions as a control unit described below. The ROM (not illustrated) stores data for control such as programs or operation parameters which are used by a processor (not illustrated). The RAM (not illustrated) temporarily stores programs and the like to be executed by a processor (not illustrated).

The recording medium (not illustrated) functions as a storage unit described below. The recording medium (not illustrated) stores, for example, data related to the control method according to the present embodiment, such as apparatus information to be described below, and various data such as various applications. Here, examples of the recording medium (not illustrated) include a magnetic recording medium such as a hard disk or a non-volatile memory such as a flash memory. In addition, the recording medium (not illustrated) may be removable from the medical observation apparatus 100.

The communication device (not illustrated) is a communication means included in the medical observation apparatus 100, and plays a role of performing wireless or wired communication with external devices such as the display apparatus 200 or the target apparatus 300. Here, examples of the communication device (not illustrated) may include an IEEE 802.15.1 port and a transmitter and receiver circuit (wireless communication), an IEEE 802.11 port and a transmitter and receiver circuit (wireless communication), a communication antenna and a radio frequency (RF) circuit (wireless communication), or a local area network (LAN) terminal, and a transmitter and receiver circuit (wired communication).

[1-3-1] Base 102

The base 102 is a base of the medical observation apparatus 100, and connected to one end of the arm 104 to support the arm 104 and the imaging device 106.

In addition, the base 102 is provided with, for example, a caster, and the medical observation apparatus 100 is in contact with a floor via the caster. By providing the caster, the medical observation apparatus 100 can easily move on the floor by the caster.

[1-3-2] Arm 104

The arm 104 is configured by connecting a plurality of links to each other with a joint.

In addition, the arm 104 also supports the imaging device 106. The imaging device 106 supported by the arm 104 is movable in three dimensions, and a position and a posture of the imaging device 106 after movement is held by the arm 104.

More specifically, the arm 104 is constituted by, for example, a plurality of joints 110a, 110b, 110c, 110d, 110e, and 110f and a plurality of links 112a, 112b, 112c, 112d, 112e, and 112f which are pivotably connected to each other by the joints 110a, 110b, 110c, 110d, 110e, and 110f. A pivotable range of each of the joints 110a, 110b, 110c, 110d, 110e, and 110f is arbitrarily set in a design stage, a manufacturing stage, or the like so that the desired movement of the arm 104 is realized.

That is, in the medical observation apparatus 100 illustrated in FIG. 1, six degrees of freedom for the imaging device 106 is realized by six rotation axes (first axis O1, second axis O2, third axis O3, fourth axis O4, fifth axis O5, and sixth axis O6) corresponding to the six joints 110a, 110b, 110c, 110d, 110e, and 110f constituting the arm 104). More specifically, in the medical observation apparatus 100 illustrated in FIG. 1, movements with six degrees of freedom of three translational degrees of freedom and three rotational degrees of freedom are realized.

Each of the joints 110a, 110b, 110c, 110d, 110e, and 110f is provided with an actuator (not illustrated), and each of the joints 110a, 110b, 110c, 110d, 110e, and 110f rotates on the corresponding rotation axes by driving an actuator (not illustrated). The driving of the actuator (not illustrated) is controlled by, for example, a processor which functions as a control unit described below or an external control apparatus (not illustrated).

Each of the joints 110a, 110b, 110c, 110d, 110e, and 110f rotates on the corresponding rotation axes by driving the actuator (not illustrated), thereby realizing various operations of the arm 104 such as extension or contraction (folding) of the arm 104.

The joint 110a has a substantially cylindrical shape, and pivotably supports the imaging device 106 (upper end portion of the imaging device 106 in FIG. 1) around a rotation axis (first axis O1) parallel with a central axis of the imaging device 106 at a distal end portion (lower end portion in FIG. 1) of the joint 110a. Here, the medical observation apparatus 100 is configured so that the first axis O1 coincides with an optical axis in the imaging device 106. That is, the imaging device 106 pivots around the first axis O1 illustrated in FIG. 1, so the captured image for medical use captured by the imaging device 106 becomes an image that is changed so as to rotate its field of view.

The link 112a is a substantially rod-shaped member, and fixedly supports the joint 110a. The link 112a extends, for example, in a direction orthogonal to the first axis O1 and is connected to the joint 110b.

The joint 110b has a substantially cylindrical shape, and pivotably supports the link 112a around the rotation axis (second axis O2) orthogonal to the first axis O1. Further, the link 112b is fixedly connected to the joint 110b.

The link 112b is a substantially rod-shaped member, and extends in a direction orthogonal to the second axis O2. In addition, the joint 110b and the joint 110c are each connected to the link 112b.

The joint 110c has a substantially cylindrical shape, and pivotably supports the link 112b around the rotation axis (third axis O3) orthogonal to each of the first axis O1 and the second axis O2. In addition, one end of the link 112c is fixedly connected to the joint 110c.

Here, when a distal end side of the arm 104 (side on which the imaging device 106 is provided) pivots around the second axis O2 and the third axis O3, the imaging device 106 can move so that the position of the imaging device 106 in the horizontal plane is changed. That is, in the medical observation apparatus 100, the rotation around the second axis O2 and the third axis O3 is controlled, so the field of view of the captured image for medical use can move in a plane.

The link 112c is a member having one end formed in a substantially cylindrical shape and the other end formed in a substantially rod shape. The joint 110c is fixedly connected to one end side of the link 112c so that the central axis of the joint 110c and the central axis of the substantially cylindrical shape coincide with each other. In addition, the joint 110d is connected to the other end side of the link 112c.

The joint 110d has a substantially cylindrical shape, and pivotably supports the link 112c around the rotation axis (fourth axis O4) orthogonal to the third axis O3. The link 112d is fixedly connected to the joint 110d.

The link 112d is a substantially rod-shaped member, and extends to be orthogonal to the fourth axis O4. One end of the link 112d is fixedly connected to the joint 110d so as to abut on a side surface of the joint 110d in a substantially cylindrical shape. In addition, the joint 110e is connected to the other end (the end opposite to the side to which the joint 110d is connected) of the link 112d.

The joint 110e has a substantially cylindrical shape, and pivotably supports one end of the link 112d around the rotation axis (fifth axis O5) parallel to the fourth axis O4. In addition, one end of the link 112e is fixedly connected to the joint 110e.

Here, the fourth axis O4 and the fifth axis O5 are rotation axes which can move the imaging device 106 in a vertical direction. The position of the imaging device 106 in the vertical direction is changed by pivoting the distal end side (the side on which the imaging device 106 is provided) of the arm 104 around the fourth axis O4 and the fifth axis O5. Thereby, it is possible to change a distance between the imaging device 106 and the observation target such as a patient's operation site by pivoting the distal end side (the side on which the imaging device 106 is provided) of the arm 104 around the fourth axis O4 and the fifth axis O5.

The link 112e is a member which is configured by combining a first member having a substantially L shape in which one side extends in the vertical direction and the other side extends in the horizontal direction, and a second member having a rod shape extending in the vertical direction from a portion of the first member extending in the horizontal direction. The joint 110e is fixedly connected to the portion of the first member of the link 112e extending in the vertical direction. In addition, the joint 110f is connected to the second member of the link 112e.

The joint 110f has a substantially cylindrical shape, and pivotably supports the link 112e around the rotation axis (sixth axis O6) parallel to the vertical direction. In addition, the link 112f is fixedly connected to the joint 110f.

The link 112f is a substantially rod-shaped member and extends in the vertical direction. The joint 110f is connected to one end of the link 112f. In addition, the other end (the end of the side opposite to the side to which the joint 110f is connected) of the link 112f is fixedly connected to the base 102.

The arm 104 has the above-described configuration, and as a result, in the medical observation apparatus 100, six degrees of freedom are realized for the movement of the imaging device 106.

The configuration of the arm 104 is not limited to the above example.

For example, each of the joints 110a, 110b, 110c, 110d, 110e, and 110f of the arm 104 may be provided with brakes for restricting the rotation of the joints 110a, 110b, 110c, 110d, 110e, and 110f, respectively. Examples of the brake according to the present embodiment include any type of brakes such as a mechanically driven brake and an electrically driven electromagnetic brake.

The driving of the brake is controlled by, for example, a processor which functions as a control unit described later or an external control apparatus (not illustrated). The driving of the brake is controlled, and as a result, an operation mode of the arm 104 is set in the medical observation apparatus 100. Examples of the operation mode of the arm 104 include a fixed mode and a free mode.

Here, the fixed mode according to the present embodiment is, for example, an operation mode in which the rotation of each rotation axis provided on the arm 104 is restricted by the brake to fix the position and posture of the imaging device 106.

In addition, the free mode according to the present embodiment is an operation mode in which each rotation axis provided on the arm 104 can freely rotate by releasing the brake. For example, in the free mode, the position and posture of the imaging device 106 can be adjusted by the direct operation of the operator. Here, the direct operation according to the present embodiment means, for example, an operation in which an operator holds the imaging device 106 by hand and directly moves the imaging device 106.

[1-3-3] Imaging Device 106

The imaging device 106 is supported by the arm 104 and images an observation target such as a patient's operation site. The capturing by the imaging device 106 is controlled by, for example, a processor which functions as a control unit described later or an external control apparatus (not illustrated).

The imaging device 106 has a configuration corresponding to, for example, an electronic imaging type microscope.

Figure 3:
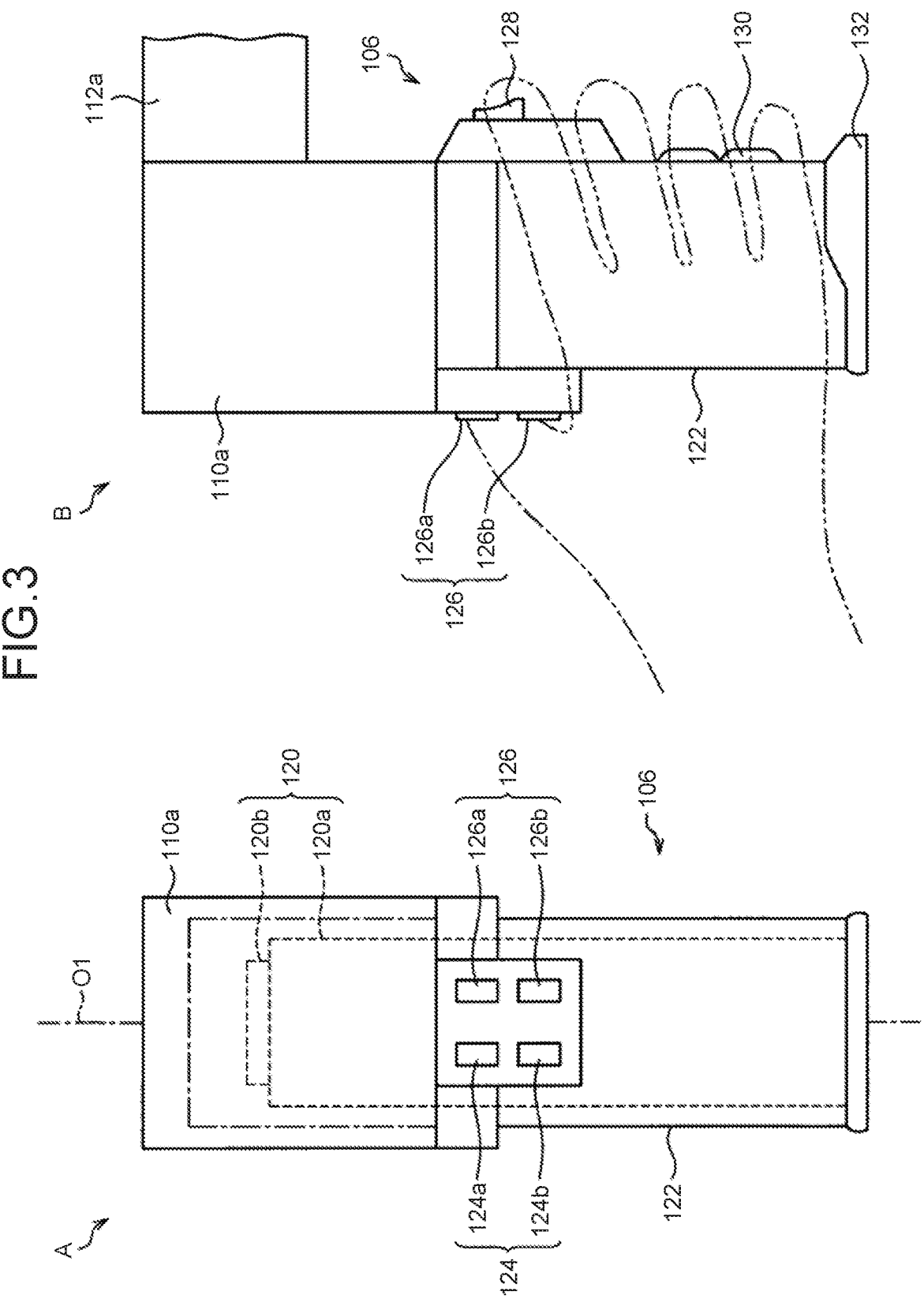
FIG. 3 is an explanatory view for explaining an example of a configuration of an imaging device included in the medical observation apparatus according to the present embodiment.

FIG. 3 is an explanatory view for explaining an example of a configuration of an imaging device 106 included in the medical observation apparatus 100 according to the present embodiment.

The imaging device 106 includes, for example, an imaging member 120 and a cylindrical member 122 having a substantially cylindrical shape, and the imaging member 120 is provided in the cylindrical member 122.

For example, a cover glass (not illustrated) for protecting the imaging member 120 is provided on an opening surface of a lower end (lower end in FIG. 3) of the cylindrical member 122.

In addition, for example, a light source (not illustrated) is provided inside the cylindrical member 122, and at the time of imaging, illumination light is irradiated to a subject from the light source through the cover glass. Reflected light (observation light) from the subject irradiated with illumination light is incident on the imaging member 120 through the cover glass (not illustrated), so an image signal (image signal indicating the captured image) indicating the subject by the imaging member 120 is obtained.

As the imaging member 120, it is possible to apply the configuration used in various known electronic imaging type microscopes.

As an example, the imaging member 120 includes, for example, an optical system 120a and an image sensor 120b which includes an imaging element imaging an image of an observation target with light passing through the optical system 120a. The optical system 120a includes, for example, one or more lenses such as an objective lens, a zoom lens, and a focus lens, and an optical element such as a mirror. Examples of the image sensor 120b include an image sensor using a plurality of imaging elements such as a complementary metal oxide semiconductor (CMOS) and a charge coupled device (CCD).

The imaging member 120 may have a configuration having a pair of imaging elements, that is, a configuration that functions as a so-called stereo camera. The imaging member 120 is generally equipped with one or more functions generally provided in an electronic imaging type microscope unit such as an auto focus (AF) function including at least a zoom function (one or both of an optical zoom function and an electronic zoom function).

In addition, the imaging member 120 may be configured to be capable of imaging at a so-called high resolution such as 4K and 8K, for example. Since the imaging member 120 is configured to be capable of capturing at high resolution, the image can be displayed on the display apparatus 200 having a large display screen such as 50 inches or more while securing a predetermined resolution (for example, Full HD image quality and the like), thereby improving visibility of an operator who looks at the display screen. In addition, the imaging member 120 is configured to be capable of imaging at high resolution, and thus it is possible to secure a predetermined resolution even if the captured image is magnified by the electronic zoom function and displayed on the display screen of the display apparatus 200. In addition, when a predetermined resolution is secured using the electronic zoom function, the performance of the optical zoom function in the imaging device 106 can be suppressed, so the optical system of the imaging device 106 can be further simplified and the imaging device 106 can be configured to be smaller.

The imaging device 106 is provided with, for example, various operation devices for controlling the operation of the imaging device 106. For example, in FIG. 3, the imaging device 106 includes a zoom switch 124, a focus switch 126, and an operation mode change switch 128. It goes without saying that positions and shapes where the zoom switch 124, the focus switch 126, and the operation mode change switch 128 are provided are not limited to the example illustrated in FIG. 3.

The zoom switch 124 and the focus switch 126 are an example of an operation device for adjusting a capturing condition in the imaging device 106.

The zoom switch 124 includes, for example, a zoom-in switch 124a for increasing a zoom magnification (magnification) and a zoom-out switch 124b for reducing a zoom magnification. By operating the zoom switch 124, the zoom magnification is adjusted to adjust the zoom.

The focus switch 126 includes, for example, a distant view focus switch 126a for increasing a focal length to the observation target (subject) and a near view focus switch 126b for reducing a focal length to the observation target. By operating the focus switch 126, the focal length is adjusted to adjust the focus.

The operation mode change switch 128 is an example of an operation device for changing the operation mode of the arm 104 in the imaging device 106. By operating the operation mode change switch 128, the operation mode of the arm 104 is changed. Examples of the operation mode of the arm 104 include the fixed mode and the free mode as described above.

Examples of the operation of the operation mode change switch 128 include an operation of pressing the operation mode change switch 128. For example, while an operator presses the operation mode change switch 128, the operation mode of the arm 104 becomes the free mode, and when an operator does not press the operation mode change switch 128, the operation mode of the arm 104 becomes the fixed mode.

In addition, the imaging device 106 is provided with, for example, an anti-slip member 130 and a protruding member 132 in order to further enhance operability and convenience when an operator who performs an operation on various operation devices performs an operation.

The anti-slip member 130 is, for example, a member provided to prevent slipping of an operating body when the operator operates the cylindrical member 122 with the operating body such as a hand. The anti-slip member 130 is formed of, for example, a material having a large coefficient of friction, and has a less slippery structure such as irregularities.

The protruding member 132 is a member which is provided to prevent the operating body from blocking the field of view of the optical system 120a when the operator operates the cylindrical member 122 with the operating body such as a hand or prevent the cover glass from being polluted due to a contact of the operating body with the cover glass (not illustrated) when the operation is performed with the operating body.

It goes without saying that a position and a shape at which the anti-slip member 130 and the protruding member 132 are each provided are not limited to the example illustrated in FIG. 3. In addition, the imaging device 106 may not be provided with one or both of the anti-slip member 130 and the protruding member 132.

An image signal (image data) generated by the capturing by the imaging device 106 is subjected to image processing, for example, by a processor that functions as a control unit described later. Examples of the image processing according to the present embodiment includes one or more of various pieces of processing such as gamma correction, adjustment of white balance, magnification or reduction of an image related to an electronic zoom function, or inter-pixel correction. When the medical observation system according to the present embodiment includes a control apparatus (not illustrated) which controls various operations in the medical observation apparatus 100, the image processing according to the present embodiment may be performed by the control apparatus (not illustrated).

The medical observation apparatus 100 transmits, for example, a display control signal and an image signal subjected to the above-described image processing to the display apparatus 200. As described later, the image signal transmitted to the display apparatus 200 is not limited to the image signal subjected to the image processing as described above.

By transmitting the display control signal and the image signal to the display apparatus 200, the captured image in which the observation target is captured (for example, the captured image in which the operation site is captured) is magnified or reduced at a predetermined magnification by one or both of the optical zoom function and the electronic zoom function and displayed on the display screen of the display apparatus 200.

The medical observation apparatus 100 has, for example, a hardware configuration illustrated in FIGS. 1 and 3.

The hardware configuration of the medical observation apparatus according to the present embodiment is not limited to the configuration illustrated in FIGS. 1 and 3.

For example, the medical observation apparatus according to the present embodiment may not include the base 102, and the arm 104 may be directly attached to a ceiling or a wall of an operating room or the like. For example, when the arm 104 is attached to the ceiling, the medical observation apparatus according to the present embodiment is configured so that the arm 104 is suspended from a ceiling.

In addition, FIG. 1 illustrates an example in which the arm 104 is configured to realize six degrees of freedom for the driving of the imaging device 106, but the configuration of the arm 104 is not limited to the configuration in which the degree of freedom for the driving of the imaging device 106 is the six degrees of freedom. For example, the arm 104 may be configured to appropriately move the imaging device 106 according to the application, and the number or arrangement of joints and links, a direction in a drive shaft of the joint and the like can be appropriately set so that the arm 104 has a desired degree of freedom.

In addition, FIGS. 1 and 3 illustrate an example in which various operation devices for controlling the operation of the imaging device 106 are provided in the imaging device 106, but some or all of the operation devices illustrated in FIGS. 1 and 3 may not be provided in the imaging device 106. As an example, various operation devices for controlling the operation of the imaging device 106 may be provided in other parts other than imaging device 106 which configures the medical observation apparatus according to the present embodiment. In addition, as another example, various operation devices for controlling the operation of the imaging device 106 may be an external operation device such as a foot switch or a remote controller.

Figure 4:
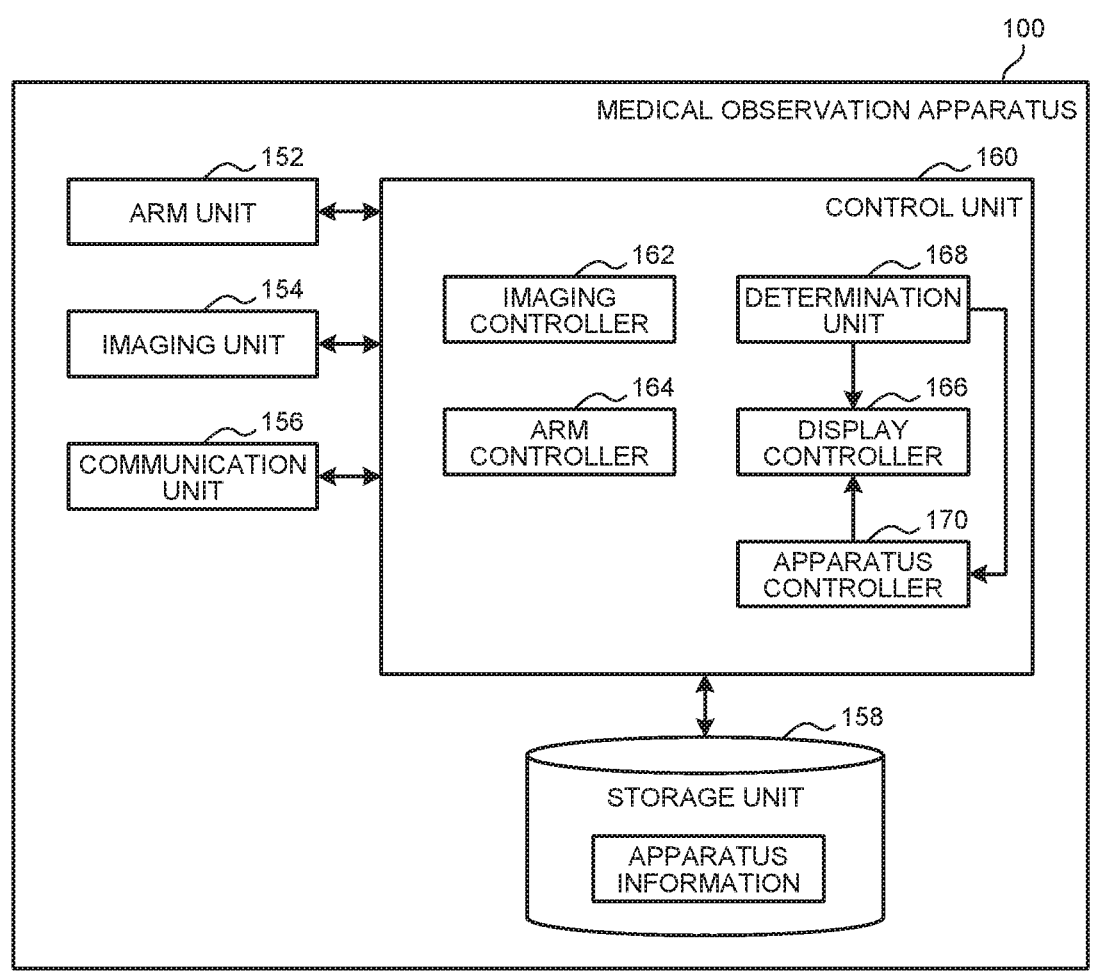
FIG. 4 is a functional block diagram illustrating an example of a configuration of the medical observation apparatus according to the present embodiment.

Next, the medical observation apparatus 100 illustrated in FIG. 1 will be described using a functional block. FIG. 4 is a functional block diagram illustrating an example of a configuration of the medical observation apparatus 100 according to the present embodiment.

The medical observation apparatus 100 includes, for example, an arm unit 152, an imaging unit 154, a communication unit 156, a storage unit 158, and a control unit 160.

The arm unit 152 is constituted by the arm 104 and supports the imaging device 106 which configures the imaging unit 154.

The imaging unit 154 is constituted by the imaging device 106, and images an observation target. The capturing by the imaging unit 154 is controlled by, for example, the control unit 160.

The communication unit 156 is communication means included in the medical observation apparatus 100, and plays a role of performing wireless or wired communication with external apparatuses such as the display apparatus 200 or the target apparatus 300. The communication unit 156 is constituted by, for example, the above-described communication device (not illustrated). The communication in the communication unit 156 is controlled by, for example, the control unit 160.

The storage unit 158 is storage means included in the medical observation apparatus 100, and stores data related to the control method according to the present embodiment, such as apparatus information or various data such as various applications. FIG. 4 illustrates an example in which the apparatus information is stored in the storage unit 158.

Here, the apparatus information according to the present embodiment is data regarding a target apparatus 300 (hereinafter, may be referred to as an "apparatus to be determined") whose use is determined by the processing related to the control method according to the present embodiment.

Examples of the apparatus information include "a table (or database) in which apparatus identification information indicating an apparatus to be determined and apparatus determination information used to determine the apparatus to be determined are stored in association with each apparatus to be determined". The apparatus information may be data for each apparatus to be determined.

Examples of the apparatus identification information according to the present embodiment include any type of data uniquely indicating an apparatus such as an apparatus ID.

Examples of the apparatus determination information according to the present embodiment include image data indicating an instrument used in the apparatus to be determined, instrument feature data indicating features of the instrument such as a shape or a color of the instrument, any type of data which can be used to identify the apparatus to be determined. The apparatus determination information may be data indicating all the instruments used in the apparatus to be determined, or may be data indicating some (for example, a distal end portion of a probe) of the instruments.

Figure 5:
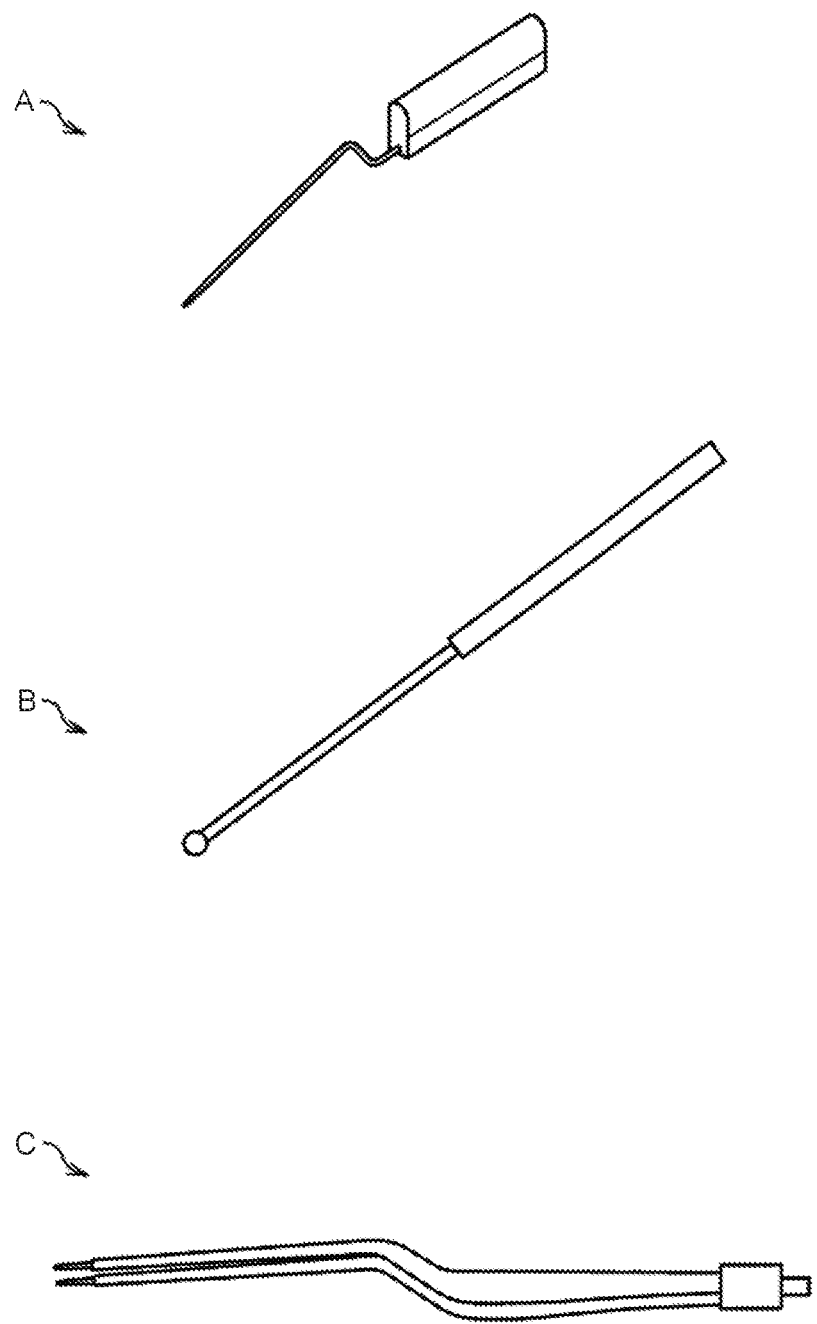
FIG. 5 is an explanatory view illustrating an example of an instrument used in an apparatus to be determined according to the present embodiment.

FIG. 5 is an explanatory view illustrating an example of an instrument used in an apparatus to be determined according to the present embodiment.

A of FIG. 5 illustrates an example of a position detection probe used in a navigation apparatus. The position detection probe corresponds to an example of an instrument used in the apparatus to be determined when the apparatus to be determined is the navigation apparatus.

B of FIG. 5 illustrates an example of a nerve stimulus probe used in a nerve monitor. The nerve stimulus probe corresponds to an example of an instrument used in the apparatus to be determined when the apparatus to be determined is the nerve monitor.

C of FIG. 5 illustrates an example of a bipolar forceps used in bipolar. The bipolar forceps corresponds to an example of an instrument used in the apparatus to be determined when the apparatus to be determined is the bipolar.

It goes without saying that the instrument used in the apparatus to be determined according to the present embodiment is not limited to the example illustrated in FIG. 5.

FIG. 6 is an explanatory view illustrating an example of apparatus determination information corresponding to an instrument used in the apparatus to be determined illustrated in FIG. 5.

A of FIG. 6 illustrates an example of an image showing the position detection probe illustrated in A of FIG. 5. B of FIG. 6 illustrates an example of an image showing the nerve stimulus probe illustrated in B of FIG. 5. C of FIG. 6 illustrates an example of an image showing the bipolar forceps illustrated in C of FIG. 5.

For example, an image showing an instrument used in the apparatus to be determined as illustrated in FIG. 6 is included in the apparatus information as the apparatus determination information. It goes without saying that as described above, the apparatus determination information is not limited to the image as illustrated in FIG. 6.

The apparatus information according to the present embodiment is not limited to the "table (or database) in which the apparatus identification information indicating the apparatus to be determined and the apparatus determination information used to determine the apparatus to be determined are stored in association with each apparatus to be determined". For example, the apparatus information according to the present embodiment may further include communication information for communicating with the apparatus to be determined. Examples of the communication information may include information indicating an address of the apparatus to be determined.

The apparatus information is stored in the storage unit 158 by performing a predetermined registration operation using, for example, an operation device included in the medical observation apparatus 100, an external operation device such as a remote controller or the like. In addition, the apparatus information is deleted from the storage unit 158 by performing a predetermined deletion operation using, for example, the operation device included in the medical observation apparatus 100, the external operation device such as a remote controller or the like.

In addition, the apparatus information may be stored in advance at the time of manufacturing the medical observation apparatus 100, or may be added, deleted, or changed at any timing such as maintenance of the medical observation apparatus 100.

Examples of the storage unit 158 include a magnetic recording medium such as a hard disk or a non-volatile memory such as a flash memory. In addition, the storage unit 158 may be removable from the medical observation apparatus 100.

The control unit 160 is constituted by, for example, the above-described processor (not illustrated), and plays a role of controlling the entire medical observation apparatus 100. In addition, the control unit 160 also plays a leading role in performing processing related to a control method to be described later. It is to be noted that the processing related to the control method in the control unit 160 may be distributed and performed by a plurality of processing circuits (for example, a plurality of processors or the like).

More specifically, the control unit 160 includes, for example, an imaging controller 162, an arm controller 164, a display controller 166, a determination unit 168, and an apparatus controller 170.

The imaging controller 162 controls the imaging device 106 that constitutes the imaging unit 154. Examples of the control of the imaging device 106 include a control of at least a zoom function (one or both of the optical zoom function and the electronic zoom function) and a control of one or more functions generally included in the electronic imaging type microscope such as a control of the AF function.

The arm controller 164 controls the driving of the arm 104 which configures the arm unit 152. Examples of the control of the driving of the arm 104 include "applying a control signal for controlling the driving to the actuator (not illustrated) corresponding to each of the joints 110a, 110b, 110c, 110d, 110e, and 110f.

The display controller 166 transmits, for example, a display control signal and an image signal to a communication device (not illustrated) configuring the communication unit 156, and transmits the display control signal and the image signal to the display apparatus 200 to control the display apparatus 200 to perform a display. The control of communication in the communication unit 156 may be performed by a communication control unit (not illustrated) configuring the control unit 160.

In addition, the display controller 166 performs display control processing (described later) in the processing related to the control method according to the present embodiment. The display controller 166 controls the display apparatus 200 to perform the display in cooperation with each of the determination unit 168 and the apparatus controller 170, as described later.

The determination unit 168 plays a role of performing apparatus determination processing (described later) in the processing related to the control method according to the present embodiment, and determines an apparatus to be used based on the captured image for medical use.

The determination result in the determination unit 168 is transmitted to the display controller 166, and the display controller 166 performs processing corresponding to the determination result. In addition, the determination result in the determination unit 168 is transmitted to the apparatus controller 170, and the apparatus controller 170 performs processing corresponding to the determination result.

The apparatus controller 170 plays a role of performing apparatus control processing (described later) in the processing related to the control method according to the present embodiment, and controls an apparatus determined by the determination unit 168.

The apparatus controller 170 transmits a control signal including a command for controlling the operation to the communication device (not illustrated) configuring the communication unit 156, and transmits a control signal to the apparatus determined by determination unit 168 to control the apparatus determined by the determination unit 168. As described above, the control of communication in the communication unit 156 may be performed by the communication controller (not illustrated) configuring the control unit 160.

The control unit 160 has, for example, a display controller 166, a determination unit 168, and an apparatus controller 170 to play a leading role in performing processing related to the control method according to the present embodiment. In addition, the control unit 160 includes, for example, the imaging controller 162, the arm controller 164, and the display controller 166 to serve to control the entire medical observation apparatus 100.

The configuration of the control unit 160 is not limited to the example illustrated in FIG. 4.

For example, the control unit 160 may not include the apparatus controller 170 which performs the apparatus control processing (described below). Even when the apparatus controller 170 is not provided, it is possible to assist the medical worker by the apparatus determination processing (described below) by the determination unit 168 and the display control processing (described below) by the display controller 166.

That is, the control unit 160 can have, for example, a configuration corresponding to the processing related to the control method according to the present embodiment executed by the medical observation apparatus 100.

In addition, the control unit 160 may have any configuration corresponding to how to separate the functions of the medical observation apparatus 100, such as a configuration corresponding to how to separate processing according to the control method according to the present embodiment.

The medical observation apparatus 100 performs processing related to the control method according to the present embodiment described below, for example, with the configuration illustrated in FIG. 4.

In addition, the configuration of the medical observation apparatus according to the present embodiment is not limited to the configuration illustrated in FIG. 4.

For example, the medical observation apparatus according to the present embodiment can include one or more of the imaging controller 162, the arm controller 164, the display controller 166, the determination unit 168, and the apparatus controller 170 illustrated in FIG. 4, separately from the control unit 160 (for example, realized by another processing circuit).

Further, the configuration for realizing the processing related to the control method according to the present embodiment in the medical observation apparatus according to the present embodiment is not limited to the configuration illustrated in FIG. 4, and can be, for example, the configuration corresponding to the processing related to the control method according to the present embodiment executed in the medical observation apparatus according to the present embodiment or the configuration corresponding to how to separate the processing related to the control method according to the present embodiment.

In addition, for example, when communicating with the external device through the external communication device having the same function and configuration as those of the communication unit 156, the medical observation apparatus according to the present embodiment may not include the communication unit 156.

In addition, when the medical observation system according to the present embodiment has the control apparatus (not illustrated) and the medical observation apparatus according to the present embodiment is controlled by the control apparatus (not illustrated), the medical observation apparatus according to the present embodiment may not include the control unit 160.

Here, the control apparatus (not illustrated) includes a control unit having the same function and configuration as those of the control unit 160 to perform the processing related to the control method according to the present embodiment described below, and furthermore, controls the operation of each component such as the arm unit 152 or the imaging unit 154 included in the medical observation apparatus according to the present embodiment. The control apparatus (not illustrated) communicates with the medical observation apparatus according to the present embodiment through the provided communication device or the connected external communication device to control the operation of each component included in the medical observation apparatus according to the present embodiment.

In addition, when the medical observation system according to the present embodiment is configured to have the control apparatus (not illustrated) and the medical observation apparatus according to the present embodiment is controlled by the control apparatus (not illustrated), the medical observation apparatus according to the present embodiment can be configured not to have some functions of the control unit 160.

In addition, the medical observation apparatus according to the present embodiment may be a surgical microscope or a surgical endoscope.

[2] Control Method according to Present Embodiment

Next, the processing related to the control method according to the present embodiment will be described. Hereinafter, the case where the medical observation apparatus 100 (more specifically, the control unit 160 which configures the medical observation apparatus 100, for example) performs the processing related to the control method according to the present embodiment will be described as an example. As described above, in the medical observation system according to the present embodiment, the processing related to the control method according to the present embodiment may also be performed by the control apparatus (not illustrated).

[2-1] Outline of Control Method According to Present Embodiment

As described above, in the medical apparatuses such as the medical imaging apparatus or the treatment apparatus, it may be necessary to perform the individual setting according to the progress of surgery. Therefore, medical workers such as an operator or a nurse need to always pay attention to the setting of the medical apparatuses, and need to set the medical apparatuses.

In addition, in the medical imaging apparatuses such as the navigation apparatus or the endoscope, each has a dedicated display apparatus, each medical imaging apparatus has a dedicated display apparatus, and an operator needs to identify each display apparatus according to the progress of surgery. In order to further improve the time and effort required to identify each display apparatus as described above, for example, "switching the images obtained from the plurality of medical imaging apparatuses on the display screen of one display apparatus" or "simultaneously displaying images obtained from the plurality of medical imaging apparatuses on the display screen of one display apparatus by picture in picture (PIP) or the like" or the like may be performed.

Here, the operation for switching images as described above or the operation for simultaneously displaying a plurality of images by the PIP or the like are appropriately performed according to the progress of the surgery. In addition, in the medical field, the operation for switching images as described above and the operation for simultaneously displaying a plurality of images by the PIP or the like are not performed by an operator but is performed by an outside staff (medical worker) such as a nurse (for example, so-called outside nurse who prepares equipment to be used) working outside an area called a so-called clean area. Since the operation for switching images or the operation for simultaneously displaying a plurality of images by the PIP or the like as described above is not an operation that a medical worker such as a nurse should perform per se, there is a possibility that the operation that the medical worker should perform per se is hindered. Therefore, when the operation for switching images or the operation for simultaneously displaying a plurality of images by the PIP or the like as described above is required, the reduction in the operation efficiency is caused from the viewpoint of the entire progress of surgery.

Therefore, the medical observation apparatus 100 to which the control method according to the present embodiment is applied determines the apparatus to be used based on the captured image for medical use captured by the imaging device 106 (apparatus determination processing). For example, the medical observation apparatus 100 determines the apparatus to be used by detecting the apparatus to be determined indicated by the apparatus information stored in a recording medium such as the storage unit 158 from the captured image for medical use.

The medical observation apparatus 100 displays a related image for medical use corresponding to the apparatus to be used which is determined in the apparatus determination processing and the captured image for medical use (display control processing). For example, as illustrated in a use case described below, the medical observation apparatus 100 displays the related image for medical use corresponding to the apparatus to be used and the captured image for medical use together. In addition, the medical observation apparatus 100 may switch and display the related image for medical use corresponding to the apparatus to be used and the captured image for medical use based on, for example, the operation of the operator (an example of the user of the medical observation apparatus 100). That is, the medical observation apparatus 100 can display one or both of the related image for medical use corresponding to the apparatus to be used and the captured image for medical use. The medical observation apparatus 100 displays the captured image for medical use and the related image for medical use on the display screen of the display apparatus 200, for example. Hereinafter, the apparatus to be used which is determined in the apparatus determination processing may be referred to as a "determined apparatus".

The related image for medical use according to the present embodiment is, for example, an image related to a medical practice performed on the observation target of the medical observation apparatus according to the present embodiment, which is captured by the medical observation apparatus according to the present embodiment.

The related image for medical use according to the present embodiment may vary depending on the determined apparatus. For example, when the determined apparatus is "a medical imaging apparatuses such as a navigation apparatus, an endoscope, and a nerve monitor", medical images (images output from the medical imaging apparatus) obtained from each of the medical imaging apparatuses can be used as the related image for medical use. In addition, when the determined apparatus is "a treatment apparatus such as an electrocautery, a bipolar, or an ultrasonic aspirator", an image indicating the setting in the treatment apparatus such as an image indicating a bipolar output value may be used as a related image for medical use. When the determined apparatus is the medical imaging apparatus, the related image for medical use may include the image indicating the setting in the medical imaging apparatus.

When displaying the captured image for medical use and the related image for medical use together, for example, the medical observation apparatus 100 displays the captured image for medical use and one or more related image for medical use in different display areas on the display screen, thereby displaying the captured image for medical use and the related image for medical use together.

As an example of the display realized by the display control processing, the medical observation apparatus 100 performs display so that the display area in which the captured image for medical use is displayed is larger than the display area in which the related image for medical use is displayed. The medical observation apparatus 100 displays, for example, the captured image for medical use on the entire display screen, and displays the related image for medical use on a part of the display screen. The medical observation apparatus 100 realizes "displaying the captured image for medical use on the entire display screen, and displaying the related image for medical use on a part of the display screen" by the PIP.

In addition, as another example of the display realized by the display control processing, the medical observation apparatus 100 will divide the display screen into a plurality of areas and displays the captured image for medical use and the related image for medical use in each area. A size of the display area in which the captured image for medical use is displayed and a size of the display area in which the related image for medical use is displayed may be the same or different.

The medical observation apparatus 100 transmits, for example, a control signal including a control command corresponding to a display method to an image mixer included in the medical observation apparatus 100, thereby generating an image signal for displaying the captured image for medical use and the related image for medical use together. In the medical observation apparatus 100, the processor (not illustrated) included in the medical observation apparatus 100 may function as the image mixer, or may include the image mixer separately from the processor (not illustrated).

Here, the medical observation apparatus 100 may generate, for example, a control command corresponding to a preset display method, or generate a control command corresponding to the display method according to the result of the apparatus determination processing. Examples of the display method according to the result of the apparatus determination processing include "setting the area in which the related image for medical use is displayed on the display screen according to the position of the area (described below) corresponding to the apparatus to be determined which is detected from the related image for medical use" and the like. As an example, the medical observation apparatus 100 sets, for example, the area in which the related image for medical use is displayed on the display screen so that the area on the display screen does not overlap with the area (described below) corresponding to the apparatus to be determined which is detected from the related image for medical use.

Note that the image mixer for generating the image signal for displaying the captured image for medical use and the related image for medical use together may be an image mixer outside the medical observation apparatus 100. When the image mixer for generating the image signal for displaying the captured image for medical use and the related image for medical use together is an external image mixer, the medical observation apparatus 100 transmits the control signal including the control command corresponding to the display method to an external image mixer, thereby generating the image signal for displaying the captured image for medical use and the related image for medical use together in the external image mixer.

When the image mixer for generating the image signal for displaying the captured image for medical use and the related image for medical use together is the image mixer included in the medical observation apparatus 100, the medical observation apparatus 100 transmits, for example, the display control signal and the image signal generated by the image mixer to the display apparatus 200. By transmitting the display control signal and the image signal to the display apparatus 200, the captured image for medical use and the related image for medical use are displayed on the display screen of the display apparatus 200 together.

In addition, when switching and displaying the captured image for medical use and the related image for medical use, the medical observation apparatus 100 displays, for example, one of the captured image for medical use or the related image for medical use in the entire display area on the display screen or a part of the display area on the display screen.

For example, when an operation signal for switching an image transmitted from an operation device included in the medical observation apparatus 100 or an external operation device such as a remote controller is detected, the medical observation apparatus 100 transmits a control signal including a control command to an image mixer to control an operation of the image mixer and transmits a display control signal and an image signal indicating one of the captured image for medical use or the related image for medical use to the display apparatus 200. The display control signal and the image signal indicating one of the captured image for medical use and the related image for medical use are transmitted to the display apparatus 200, so one of the captured image for medical use and the related image for medical use are displayed on the display screen of the display apparatus 200. In addition, the switching of the captured image for medical use and the related image for medical use is realized by "switching the image signal received by the display apparatus 200 from the image signal indicating the captured image for medical use to the image signal indicating the related image for medical use", or "switching the image signal received by the display apparatus 200 from the image signal indicating the related image for medical use to the image signal indicating the captured image for medical use.

By using the medical observation apparatus 100 to which the control method according to the present embodiment is applied, when the apparatus to be determined is detected from the captured image for medical use, the related image for medical use corresponding to the apparatus to be determined is displayed on the display screen together with the captured image for medical use. Therefore, when a medical observation system 1000 including a medical observation apparatus 100 is used, an operator does not need to distinguish a dedicated display apparatus of a medical imaging apparatus according to the progress of surgery, and a medical worker such as a nurse does not need to appropriately perform an operation for switching an image and the like.

In addition, for example, the operator performs an operation of switching images using an operation device and the like included in the medical observation apparatus 100 and thus can switch the related image for medical use corresponding to the apparatus to be used and the captured image for medical use.

Therefore, by using the medical observation apparatus 100 to which the control method according to the present embodiment is applied, it is possible to assist a medical worker such as an operator or a nurse.

The processing related to the control method according to the present embodiment is not limited to the apparatus determination processing and the display control processing.

For example, the medical observation apparatus 100 may further control the apparatus determined in the apparatus determination processing (apparatus control processing).

The medical observation apparatus 100 controls the determined apparatus by causing the communication unit 156 or an external communication device to transmit a control signal including a command for performing the processing to the determined apparatus. For example, the medical observation apparatus 100 generates the control signal based on an operation on the operation device included in the medical observation apparatus 100 or an external operation device such as a remote controller and transmits the generated control signal to the determined apparatus.

As an example of the control of the apparatus determined by the apparatus control processing, for example, when the determined apparatus is "a medical imaging apparatus such as a navigation apparatus, an endoscope, a nerve monitor", the medical observation apparatus 100 changes the medical image output from the medical imaging apparatus. Examples of the change in the medical image output from the medical imaging apparatus include a change to any medical image which the medical imaging apparatus can output, such as a change in a size of the output medical image, a change in content of the output medical image, and a change in a layout of the output medical image.

In addition, as another example of the control of the apparatus determined by the apparatus control processing, for example, when the determined apparatus is "treatment apparatuses such as an electrocautery, a bipolar, or an ultrasonic aspirator", the medical observation apparatus 100 changes the settings of the treatment apparatus, such as the bipolar output value. The apparatus whose setting can be changed by the medical observation apparatus 100 is not limited to the treatment apparatus, and the medical observation apparatus 100 can also change the setting of the medical imaging apparatus.

The medical observation apparatus 100 further performs the apparatus control processing as the processing related to the control method according to the present embodiment, and for example, the operator operates the operation device or the like included in the medical observation apparatus 100, such that the settings of various medical apparatuses such as "an electrocautery, a bipolar, or an ultrasonic aspirator" can be appropriately changed according to the progress of surgery.

As a result, the medical observation apparatus 100 can further assist medical workers such as an operator by further performing the apparatus control processing as the processing related to the control method according to the present embodiment.

[2-2] Processing Related to Control Method According to Present Embodiment

Next, the processing related to the control method according to the present embodiment will be described in more detail.

As described above, examples of the processing related to the control method according to the present embodiment include "apparatus determination processing and display control processing" or "apparatus determination processing, display control processing, and apparatus control processing". Hereinafter, the apparatus determination processing, the display control processing, and the apparatus control processing will each be described. The apparatus determination processing, the display control processing, and the apparatus control processing are divided into processing related to the control method according to the present embodiment for the sake of convenience, and the method of dividing the processing related to the control method according to the present embodiment is not limited to the "apparatus determination processing and display control processing" or the "apparatus determination processing, display control processing, and apparatus control processing".

In addition, the processing related to the control method according to the present embodiment is automatically performed in the case where the medical observation apparatus 100 is in a predetermined state, such as the case where a power supply of the medical observation apparatus 100 is in a turned on state or the case where the capturing is performed by the imaging device 106 of the medical observation apparatus 100. In addition, the processing related to the control method according to the present embodiment may be started and terminated based on the operation on the operation device included in the medical observation apparatus 100 or the external operation device such as a foot switch or a remote controller. That is, in the medical observation apparatus 100, the processing related to the control method according to the present embodiment may be performed automatically, or may be performed based on an operation of a user such as an operator.

(1) Apparatus Determination Processing

The medical observation apparatus 100 determines an apparatus to be used based on the captured image for medical use captured by the imaging device 106.

For example, the medical observation apparatus 100 determines an apparatus to be used every time the capturing is performed by the imaging device 106. Here, every time the imaging device 106 performs the imaging, for example, when the imaging device 106 captures the moving image, "every frame" is indicated, and when the imaging device 106 captures a still image, and "every time the still image is captured" is indicated.

The medical observation apparatus 100 may determine an apparatus to be used periodically, for example, every predetermined frame, every predetermined time or the like. In addition, the medical observation apparatus 100 can also determine, for example, an apparatus to be used irregularly.

The medical observation apparatus 100 determines the apparatus to be used by detecting an area corresponding to the apparatus to be determined from the captured image for medical use based on the apparatus information. The medical observation apparatus 100 detects the area corresponding to the apparatus to be determined from the captured image for medical use for each apparatus to be determined.

More specifically, for example, as illustrated in A to C of FIG. 6, the medical observation apparatus 100 may compare an image (an example of apparatus determination information) indicating an instrument used in the apparatus to be determined with the captured image for medical use to detect an area including an instrument used in the apparatus to be determined. The medical observation apparatus 100 uses any method such as a template-matching method which can detect an area including an instrument used in the apparatus to be determined from the captured image for medical use to detect the area.

In addition, when the apparatus determination information is instrument feature data indicating the feature of the instrument such as the shape and color of the instrument used in the apparatus to be determined, the medical observation apparatus 100 may detect, for example, an area including a feature indicated by the instrument feature data from the captured image for medical use. The medical observation apparatus 100 extracts, for example, features corresponding to the features indicated by the instrument feature data from the captured image for medical use and compares the extracted features with the shape indicated by the instrument feature data to detect the area including the features indicated by the instrument feature data from the captured image for medical use. As an example, the medical observation apparatus 100 generates an edge image from the captured image for medical use, extracts a shape of an object included in the captured image for medical use, and compares the extracted shape with the shape indicated by the instrument feature data to detect the area including the features indicated by the instrument feature data from the captured image for medical use.

When the area including the instrument used in the apparatus to be determined is detected from the captured image for medical use, the medical observation apparatus 100 specifies, for example, the apparatus identification information associated with the "apparatus determination information corresponding to the instrument included in the detected area" from the apparatus information, and determines that the apparatus indicated by the specified apparatus identification information is the apparatus to be used. In addition, when the area is not detected from the captured image for medical use, the medical observation apparatus 100 does not determine the apparatus to be used.

For example, as in the example described above, the medical observation apparatus 100 determines the apparatus to be used by detecting the area corresponding to the apparatus to be determined from the captured image for medical use based on the apparatus information. It goes without saying that the example of the processing of determining the apparatus to be used based on the apparatus information is not limited to the example described above.

(2) Display Control Processing

The medical observation apparatus 100 displays the related image for medical use corresponding to the apparatus determined in the apparatus determination processing and the captured image for medical use. As described above, the medical observation apparatus 100 displays, for example, the related image for medical use corresponding to the apparatus to be used and the captured image for medical use together. In addition, as described above, the medical observation apparatus 100 may switch and display the related image for medical use corresponding to the apparatus to be used and the captured image for medical use based on, for example, the operation of the operator and the like.

When it is determined that the number of apparatuses used in the apparatus determination processing is one, the medical observation apparatus 100 displays one or more related images for medical use corresponding to one determined apparatus. In addition, when it is determined that the number of apparatuses to be used in the apparatus determination processing are plural, the medical observation apparatus 100 displays the related image for medical use corresponding to each of the plurality of determined apparatuses.

In addition, when the apparatus control processing is performed, the medical observation apparatus 100 displays the related image for medical use corresponding to the control of the determined apparatus. That is, the related image for medical use displayed by the medical observation apparatus 100 may be changed according to the control in the apparatus control processing.

An example of the display realized by the display control processing is shown in the use case described below.

(3) Apparatus Control Processing

The medical observation apparatus 100 controls the apparatus determined in the apparatus determination processing.

As described above, the medical observation apparatus 100 controls the determined apparatus by causing the communication unit 156 to transmit a control signal including an instruction for performing the processing to the determined apparatus. For example, the medical observation apparatus 100 transmits the control signal from the apparatus information stored in the recording medium such as the storage unit 158 to the determined apparatus using the communication information corresponding to the apparatus determined in the apparatus determination processing.

[2-3] Use Case Realized by Processing Related to Control Method According to Present Embodiment Next, a use case realized by the processing related to the control method according to the present embodiment will be described. Hereinafter, the use case in the case where the related image for medical use and the captured image for medical use are displayed together by the processing related to the control method according to the present embodiment is illustrated. It goes without saying that the use case realized by the processing related to the control method according to the present embodiment is not limited to the following example.

[2-3-1] First Example of Use Case

Figure 7:
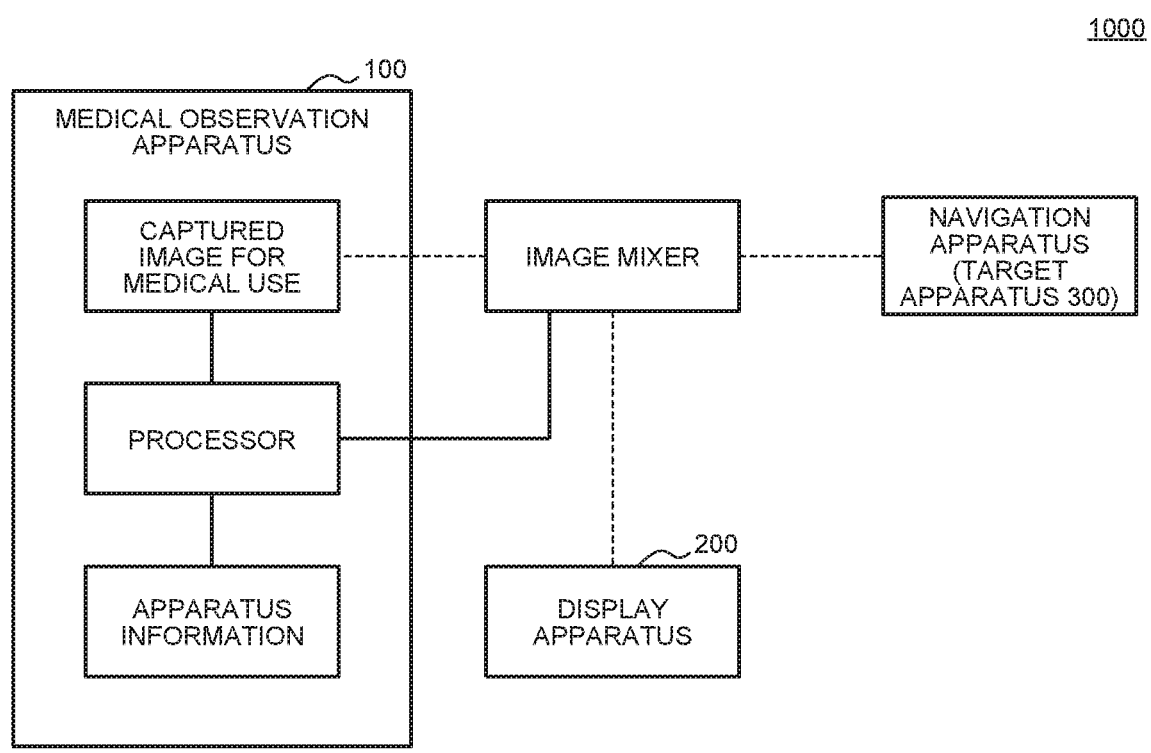
FIG. 7 is an explanatory diagram for describing a first example of a use case realized by processing related to a control method according to the present embodiment.

FIG. 7 is an explanatory diagram for explaining a first example of a use case realized by processing related to a control method according to the present embodiment, and illustrates an example of a configuration of a medical observation system 1000. FIG. 7 illustrates an example in which the target apparatus 300 is the navigation apparatus. In addition, FIG. 7 illustrates an example in which an image mixer is an image mixer outside a medical observation apparatus 100, but as described above, the image mixer may be included in the medical observation apparatus 100.

In addition, FIG. 8 is an explanatory view illustrating an example of an image displayed on a display screen of a display apparatus 200 in the first example of the use case realized by processing related to a control method according to the present embodiment. "G1" illustrated in FIG. 8 illustrates an example of a captured image for medical use, and "G2" illustrated in FIG. 8 illustrates an example of a related image for medical use obtained from a navigation apparatus. In addition, "O" illustrated in FIG. 8 illustrates a part of a position detection probe used in the navigation apparatus illustrated in A of FIG. 5.

[2-3-1-1] Action According to First Example of Use Case

For example, when an operator moves a position detection probe used in a navigation apparatus into an imaging field of view of the imaging device 106 of the medical observation apparatus 100, for example, the image illustrated in A of FIG. 8 is displayed on the display screen of the display apparatus 200.

When an area corresponding to the position detection probe used in the navigation apparatus is detected from the captured image for medical use by the apparatus determination processing based on the captured image for medical use and the apparatus information, the processor included in the medical observation apparatus 100 transmits a control signal to the image mixer.

The image mixer generates an image signal for displaying the captured image for medical use and the related image for medical use obtained from the navigation apparatus together based on the control signal, and outputs the generated image signal to the display apparatus 200.

Therefore, for example, as illustrated in B of FIG. 8, the captured image for medical use and the related image for medical use obtained from the navigation apparatus are displayed on the display screen of the display apparatus 200 together without a medical worker such as an operator or a nurse performing any switching operation.

[2-3-1-2] Effect According to First Example of Use Case

In the first example of the use case, for example, the following effects are achieved.

If the medical imaging apparatus other than the medical observation apparatus 100 is used during surgery, an operator does not perform any switching operation, and can cause the related image for medical use and the captured image for medical use obtained from the medical imaging apparatus to be displayed on the display screen simultaneously. Therefore, since the troublesome operation during surgery like the switching operation becomes unnecessary, the improvement in surgery efficiency is achieved.

In the above description, an example in which the medical imaging apparatus is the navigation apparatus is illustrated, but when other medical imaging apparatuses such as an endoscope and a nerve monitor are used, the same effects as the first example of the use case are achieved.

[2-3-2] Second Example of Use Case

Figure 9:
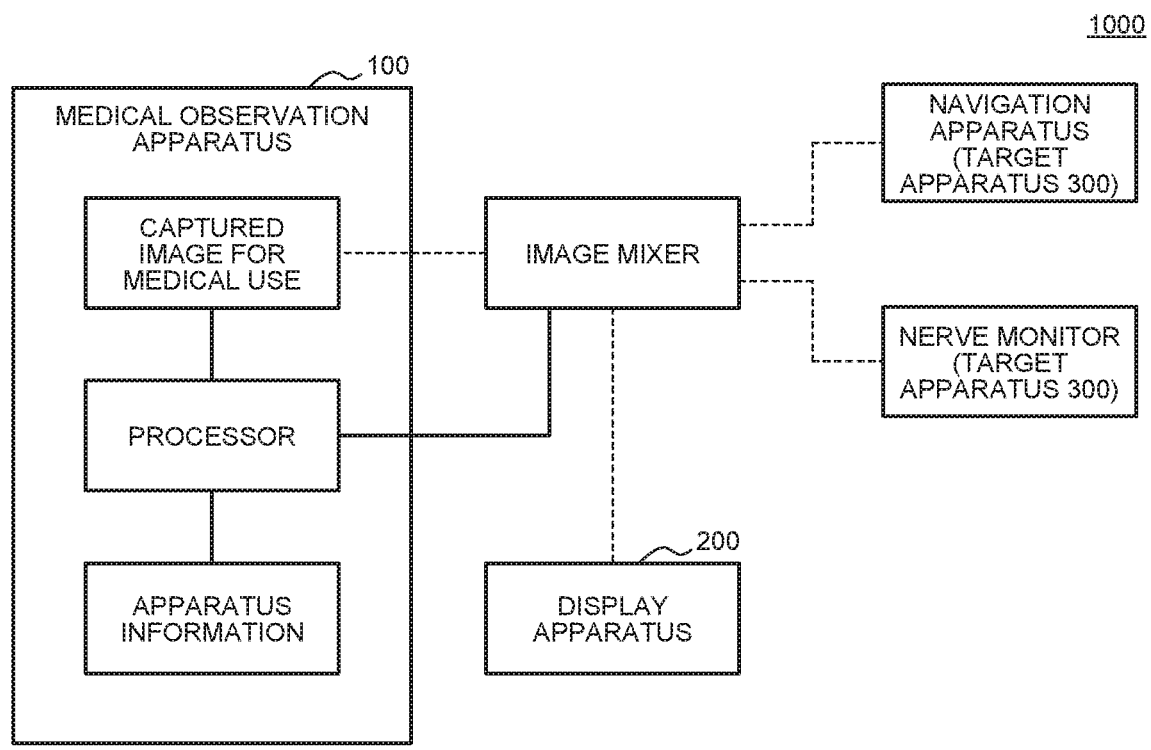
FIG. 9 is an explanatory diagram for describing a second example of a use case realized by the processing related to the control method according to the present embodiment.

FIG. 9 is an explanatory diagram for explaining a second example of a use case realized by processing related to a control method according to the present embodiment, and illustrates an example of a configuration of a medical observation system 1000. FIG. 9 illustrates an example in which the target apparatus 300 is the navigation apparatus and the nerve monitor. In addition, as in FIG. 7, FIG. 9 illustrates an example in which an image mixer is an image mixer outside a medical observation apparatus 100.

Figure 10:
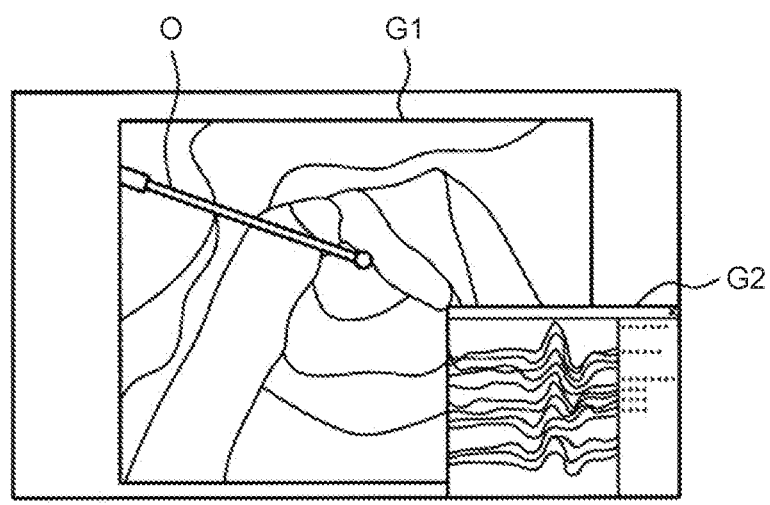
FIG. 10 is an explanatory view illustrating an example of an image displayed on a display screen of a display apparatus in the second example of the use case realized by the processing related to the control method according to the present embodiment.

In addition, FIG. 10 is an explanatory view illustrating an example of an image displayed on a display screen of a display apparatus 200 in the second example of a use case realized by processing related to a control method according to the present embodiment. "G1" illustrated in FIG. 10 illustrates an example of a captured image for medical use, and "G2" illustrated in FIG. 10 illustrates an example of a related image for medical use obtained from a nerve monitor. In addition, "O" illustrated in FIG. 10 illustrates a part of a nerve stimulus probe used in the nerve monitor illustrated in B of FIG. 5.

Figure 11:
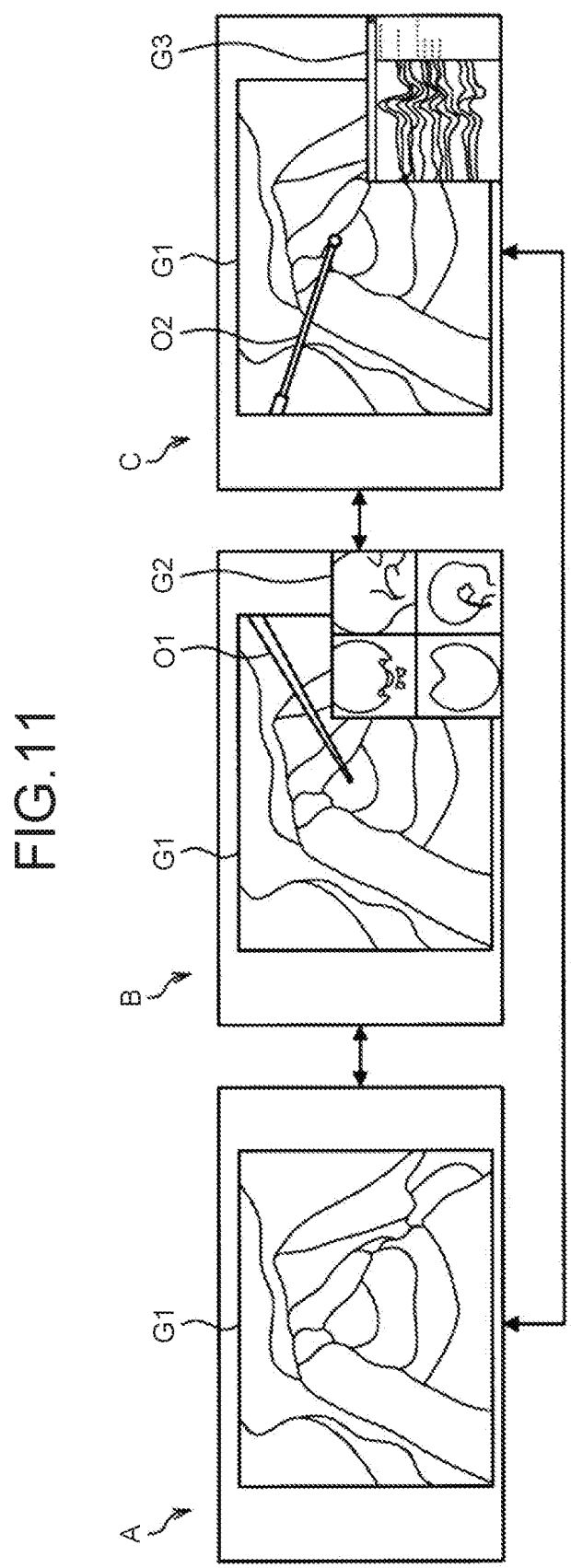
FIG. 11 is an explanatory view illustrating another example of the image displayed on the display screen of the display apparatus in the second example of the use case realized by the processing related to the control method according to the present embodiment.

In addition, FIG. 11 is an explanatory view illustrating another example of an image displayed on a display screen of a display apparatus 200 in the second example of a use case realized by processing related to a control method according to the present embodiment. "G1" illustrated in FIG. 11 indicates an example of the captured image for medical use. In addition, "G2" illustrated in FIG. 11 illustrates an example of the related image for medical use obtained from the navigation apparatus, and "G3" illustrated in FIG. 11 illustrates an example of the related image for medical use obtained from the nerve monitor. In addition, "O1" illustrated in FIG. 11 illustrates a part of the position detection probe used in the navigation apparatus illustrated in A of FIG. 5 and "O2" illustrated in FIG. 11 illustrates a part of the nerve stimulus probe used in the nerve monitor illustrated in B of FIG. 5.

[2-3-2-1] Action According to Second Example of Use Case

For example, when an operator moves the nerve stimulus probe used in the nerve monitor into the imaging field of view of the imaging device 106 of the medical observation apparatus 100, the processor of the medical observation apparatus 100 detects the area corresponding to the nerve stimulus probe used in the nerve monitor by the apparatus determination processing from the captured image for medical use based on the captured image for medical use and the apparatus information.

Therefore, for example, as illustrated in FIG. 10, the captured image for medical use and the related image for medical use obtained from the nerve monitor are displayed on the display screen of the display apparatus 200 together without a medical worker such as an operator or a nurse performing any switching operation.

In addition, as illustrated in FIG. 9, when there are a plurality of target apparatuses 300, the operator moves an instrument corresponding to the target apparatus 300 into the imaging field of view of the imaging device 106 of the medical observation apparatus 100 to switch the display on the display screen of the display apparatus 200.

This is illustrated with reference to FIG. 11. For example, when there is no instrument corresponding to the target apparatus 300 into the imaging field of view of the imaging device 106, as illustrated in A of FIG. 11, only the captured image for medical use is displayed on the display screen of the display apparatus 200.

In addition, in the state illustrated in A of FIG. 11, when the operator moves the position detection probe used in the navigation apparatus into the imaging field of view of the imaging device 106 of the medical observation apparatus 100, as illustrated in B of FIG. 11, the display screen of the display apparatus 200 is switched to a display on which the captured image for medical use and the related image for medical use obtained from the navigation apparatus are displayed together.

In addition, in the state illustrated in A of FIG. 11, when the operator moves the nerve stimulus probe used in the nerve monitor into the imaging field of view of the imaging device 106 of the medical observation apparatus 100, as illustrated in C of FIG. 11, the display screen of the display apparatus 200 is switched to a display on which the captured image for medical use and the related image for medical use obtained from the nerve monitor are displayed together.

In addition, in the state illustrated in B of FIG. 11, when the operator changes an instrument present in the imaging view of field of the imaging device 106 of the medical observation apparatus 100 from the position detection probe used in the navigation apparatus to the nerve stimulus probe used in the nerve monitor, as illustrated in C of FIG. 11, the display screen of the display apparatus 200 is switched to a display on which the captured image for medical use and the related image for medical use obtained from the nerve monitor are displayed together.

In addition, in the state illustrated in C of FIG. 11, when the operator changes the instrument present in the imaging view of field of the imaging device 106 of the medical observation apparatus 100 from the nerve stimulus probe used in the nerve monitor to the position detection probe used in the navigation apparatus, as illustrated in B of FIG. 11, the display screen of the display apparatus 200 is switched to a display on which the captured image for medical use and the related image for medical use obtained from the navigation apparatus are displayed together.

In addition, in the state illustrated in B of FIG. 11 or the state illustrated in C of FIG. 11, when the operator moves an instrument present in the imaging field of view of the imaging device 106 of the medical observation apparatus 100 out of the imaging field of view, as illustrated in A of FIG. 11, the display screen of the display apparatus 200 is switched to a display in which only the captured image for medical use is displayed.

Although not illustrated in FIG. 11, when the operator can move both the position detection probe used in the navigation apparatus and the nerve stimulus probe used in the nerve monitor into the imaging field of view of the imaging device 106 of the medical observation apparatus 100, the captured image for medical use, the related image for medical use obtained from the navigation apparatus, and the related image for medical use obtained from the nerve monitor are displayed on the display screen of the display apparatus 200 together.

[2-3-2-2] Effect According to Second Example of Use Case

In the second example of the use case, for example, the following effects are achieved.

Even when the number of medical imaging apparatuses used is increased during surgery, an operator does not perform any switching operation, and can cause the captured image for medical use and the related image for medical use obtained from the medical imaging apparatus to be displayed on the display screen simultaneously. Therefore, since the troublesome operation during surgery like the switching operation becomes unnecessary, the improvement in surgery efficiency is achieved.

In the above description, an example in which the medical imaging apparatus is the navigation apparatus and the nerve monitor is illustrated, but when other medical imaging apparatuses such as the endoscope and the nerve monitor are used and when the number of medical imaging apparatuses is three or more, the same effects as the second example of the use case are achieved.

[2-3-3] Third Example of Use Case

Figure 12:
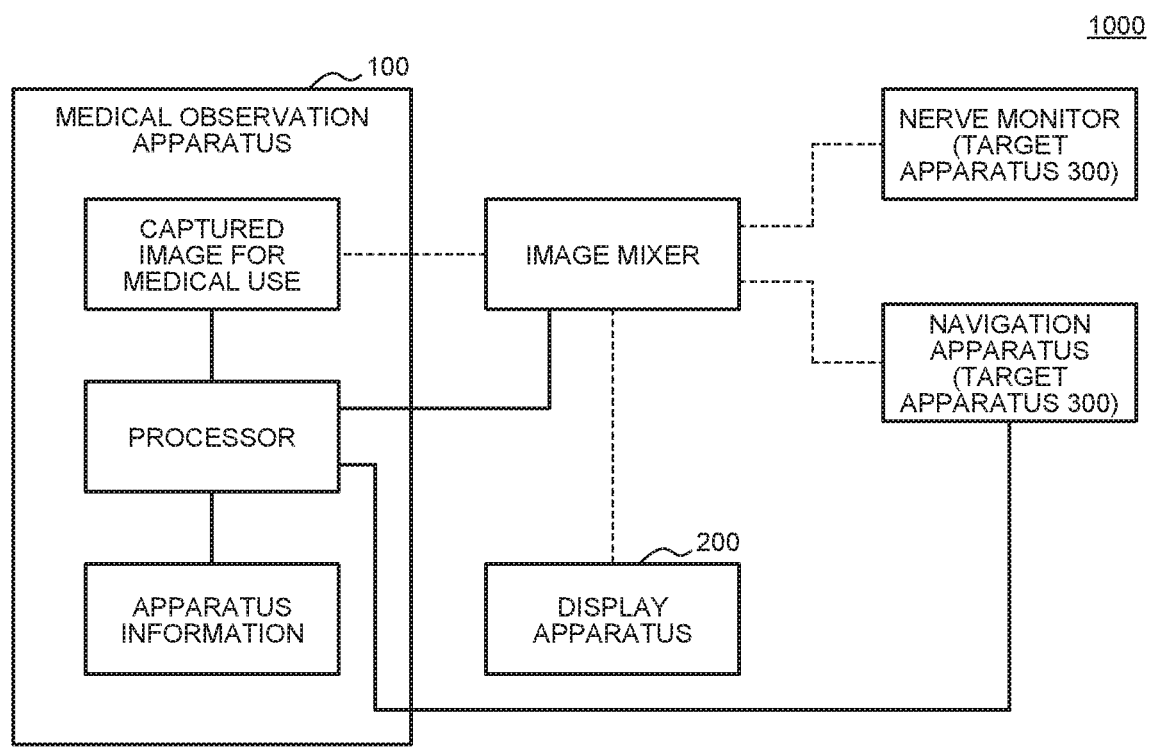
FIG. 12 is an explanatory diagram for describing a third example of a use case realized by the processing related to the control method according to the present embodiment.

FIG. 12 is an explanatory diagram for explaining a third example of a use case realized by processing related to a control method according to the present embodiment, and illustrates an example of a configuration of a medical observation system 1000. As in FIG. 9, FIG. 12 illustrates an example in which the target apparatus 300 is the navigation apparatus and the nerve monitor. In addition, as in FIG. 7, FIG. 12 illustrates an example in which an image mixer is an image mixer outside a medical observation apparatus 100.

The medical observation system 1000 illustrated in FIG. 12 has basically the same configuration as the medical observation system 1000 according to the second example of the use case illustrated in FIG. 9, but is different from the medical observation system 1000 according to the second example of the use case illustrated in FIG. 9 in that the processor of the medical observation apparatus 100 performs the apparatus control processing to be able to control the navigation apparatus.

Figure 13:
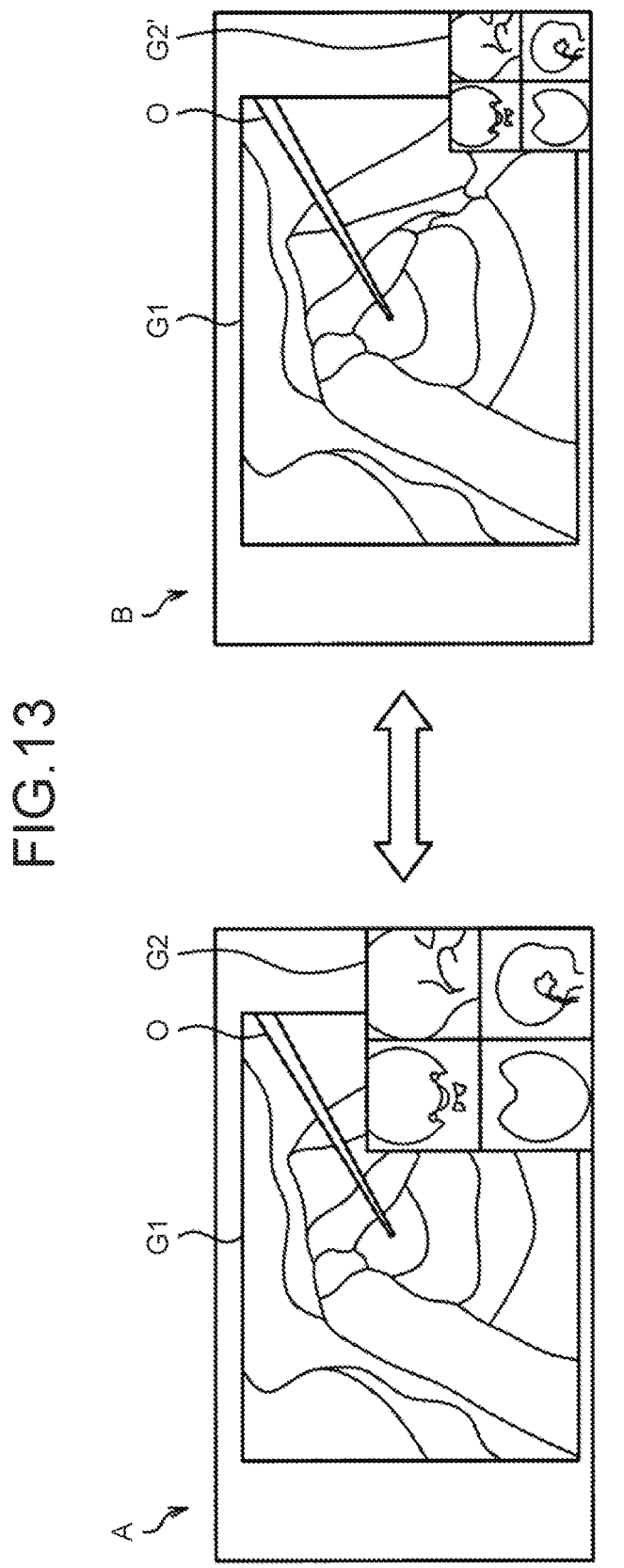
FIG. 13 is an explanatory view illustrating an example of an image displayed on a display screen of a display apparatus in the third example of the use case realized by the processing related to the control method according to the present embodiment.

In addition, FIG. 13 is an explanatory view illustrating an example of an image displayed on a display screen of a display apparatus 200 in the third example of a use case realized by processing related to a control method according to the present embodiment. "G1" illustrated in FIG. 13 indicates an example of the captured image for medical use. In addition, "G2" illustrated in FIG. 13 illustrates an example of the related image for medical use obtained from the navigation apparatus, and "G2'" illustrated in FIG. 13 illustrates another example of the related image for medical use obtained from the navigation apparatus. In addition, "O" illustrated in FIG. 13 illustrates a part of a position detection probe used in the navigation apparatus illustrated in B of FIG. 5.

Figure 14:
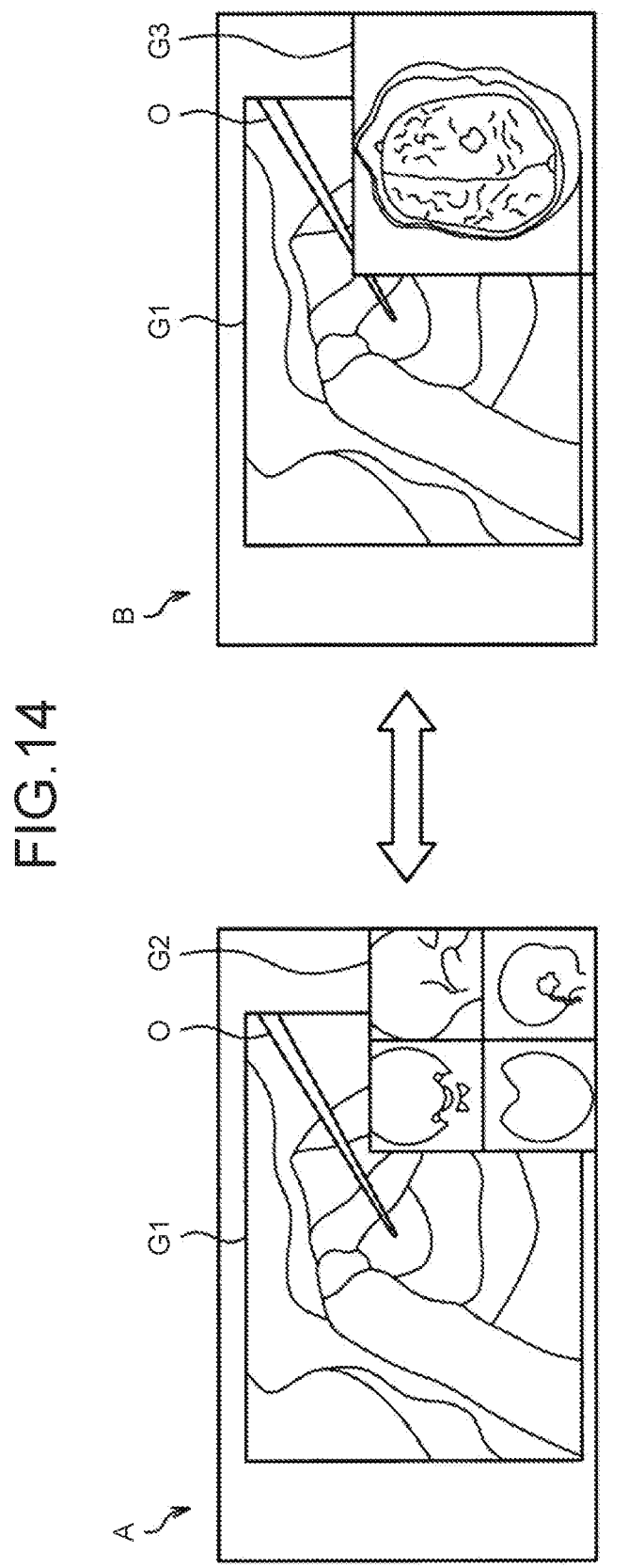
FIG. 14 is an explanatory view illustrating another example of the image displayed on the display screen of the display apparatus in the third example of the use case realized by the processing related to the control method according to the present embodiment.

In addition, FIG. 14 is an explanatory view illustrating another example of an image displayed on a display screen of a display apparatus 200 in the third example of a use case realized by processing related to a control method according to the present embodiment. "G1" illustrated in FIG. 14 indicates an example of the captured image for medical use. In addition, "G2" illustrated in FIG. 14 illustrates an example of the related image for medical use obtained from the navigation apparatus, and "G3" illustrated in FIG. 14 illustrates another example of the related image for medical use obtained from the navigation apparatus. In addition, "O" illustrated in FIG. 14 illustrates a part of a position detection probe used in the navigation apparatus illustrated in B of FIG. 5.

[2-3-3-1] Action According to Third Example of Use Case

As described above, the medical observation system 1000 illustrated in FIG. 12 has basically the same configuration as the medical observation system 1000 according to the second example of the use case illustrated in FIG. 9. Therefore, for example, when the operator moves the position detection probe used in the navigation apparatus into the imaging field of view of the imaging device 106 of the medical observation apparatus 100, as illustrated in A of FIG. 13 or A of FIG. 14, the captured image for medical use and the related image for medical use obtained from the navigation apparatus are displayed together.

For example, in a state in which the captured image for medical use and the related image for medical use obtained from the navigation apparatus are displayed together, when the operator performs an operation for controlling the navigation apparatus using the operation device or the like included in the medical observation apparatus 100, the processor of the medical observation apparatus 100 transmits the control signal corresponding to the operation to the navigation apparatus.

The navigation apparatus receiving the control signal changes the related image for medical use to be output according to the received control signal. By changing the related image for medical use output from the navigation apparatus according to the control signal, for example, the display of the display screen of the display apparatus 200 is switched to a display as in an example illustrated below from the display illustrated in A of FIG. 13 or A of FIG. 14.

The related image for medical use whose size is changed is displayed together with the captured image for medical use (B of FIG. 13).

Different related images for medical use are displayed together with the captured image for medical use (B of FIG. 14). Examples of switching of the related image for medical use output from the navigation apparatus include "switching of 3 screen display of Sagittal, Axial, Clonal and 3D generated image" and the like.

[2-3-3-2] Effect According to Third Example of Use Case

In the third example of the use case, for example, the following effects are achieved.

In addition to the effects achieved in the second example of the use case described above, the medical observation apparatus 100 can perform the control of the related image for medical use output from the medical imaging apparatus, such that the image adjustment is easily and quickly performed during surgery and the operation efficiency can be further improved.

Although the example in which the medical observation apparatus 100 controls the navigation apparatus has been described above, similarly, the medical observation apparatus 100 can control other medical apparatuses configuring the medical observation system 1000 such as the nerve monitor.

[2-3-4] Fourth Example of Use Case

Figure 15:
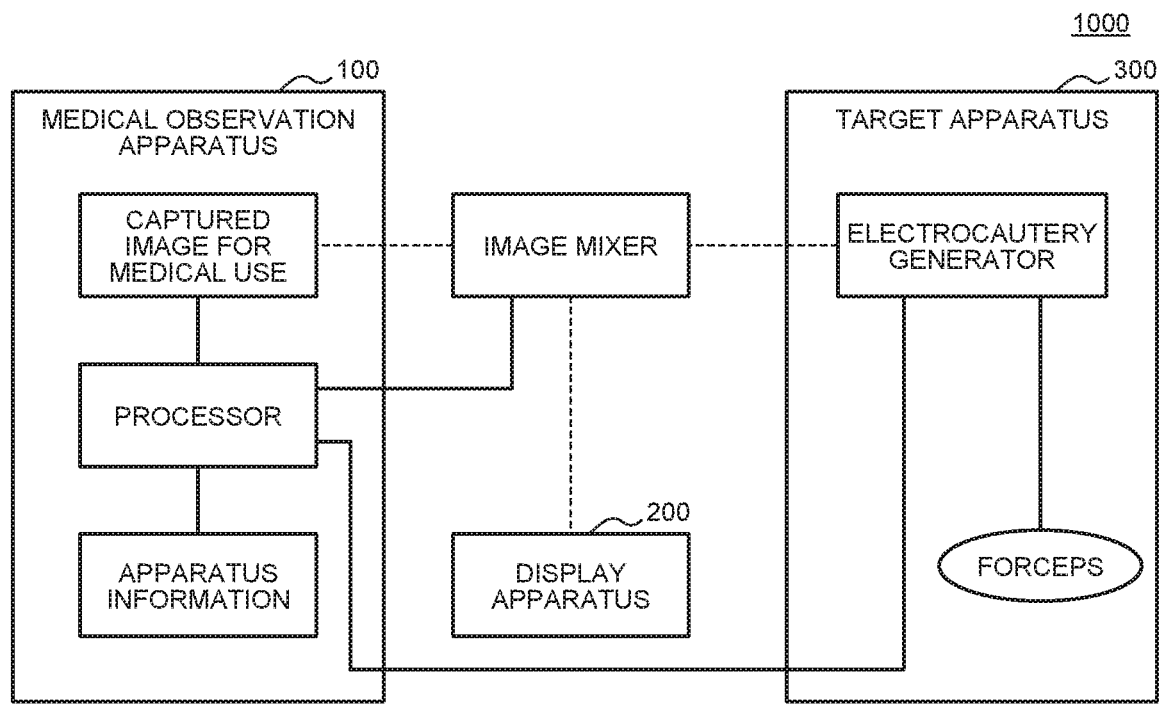
FIG. 15 is an explanatory diagram for describing a fourth example of a use case realized by the processing related to the control method according to the present embodiment.

FIG. 15 is an explanatory diagram for explaining a fourth example of a use case realized by processing related to a control method according to the present embodiment, and illustrates an example of a configuration of a medical observation system 1000. FIG. 15 illustrates an example in which the target apparatus 300 is a bipolar (an example of a treatment apparatus) which is a kind of therapeutic device (energy device). In addition, as in FIG. 7, FIG. 15 illustrates an example in which an image mixer is an image mixer outside a medical observation apparatus 100.

In the medical observation system 1000 illustrated in FIG. 15, the processor of the medical observation apparatus 100 can control an electrocautery generator which configures a bipolar by performing the apparatus control processing.

Figure 16:
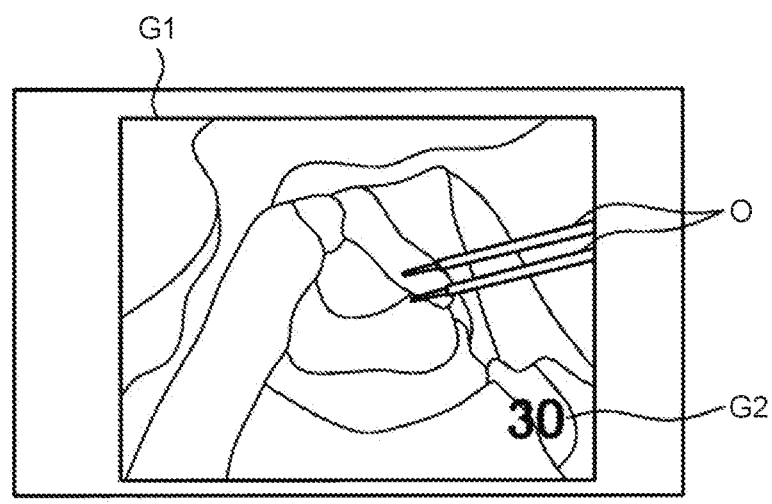
FIG. 16 is an explanatory view illustrating an example of an image displayed on a display screen of a display apparatus in the fourth example of the use case realized by the processing related to the control method according to the present embodiment.

In addition, FIG. 16 is an explanatory view illustrating an example of an image displayed on a display screen of a display apparatus 200 in the fourth example of a use case realized by processing related to a control method according to the present embodiment. "G1" illustrated in FIG. 16 illustrates an example of a captured image for medical use, and "G2" illustrated in FIG. 16 illustrates an example of a related image for medical use indicating a bipolar output value of a bipolar. In addition, "O" illustrated in FIG. 16 illustrates a part of a bipolar forceps used in the bipolar illustrated in C of FIG. 5.

[2-3-4-1] Action According to Fourth Example of Use Case

For example, when an operator moves the bipolar forceps used in the bipolar into the imaging field of view of the imaging device 106 of the medical observation apparatus 100, the processor of the medical observation apparatus 100 detects the area corresponding to the bipolar forceps used in the bipolar from the captured image for medical use by the apparatus determination processing based on the captured image for medical use and the apparatus information.

Therefore, for example, as illustrated in FIG. 16, the captured image for medical use and the related image for medical use indicating the bipolar output value of the bipolar are displayed on the display screen of the display apparatus 200 together without a medical worker such as an operator or a nurse performing any switching operation.

In addition, for example, in a state in which the captured image for medical use and the related image for medical use indicating the bipolar output value of the bipolar are displayed together, when the operator performs an operation for controlling the bipolar using the operation device or the like included in the medical observation apparatus 100, the external operation device such as a foot switch or the like, the processor of the medical observation apparatus 100 transmits the control signal corresponding to the operation to the electrocautery generator configuring the bipolar.

The electrocautery generator configuring the bipolar receiving the control signal changes the output value according to the received control signal. By changing the output value of the electrocautery generator according to the control signal, the bipolar output value indicated by the related image for medical use displayed on the display screen of the display apparatus 200 is changed to the value after the change.

[2-3-4-2] Effect According to Fourth Example of Use Case

In the fourth example of the use case, for example, the following effects are achieved.

The therapeutic device such as the bipolar as well as the first example of the use case to the medical imaging apparatus as in the third example of the use case is also determined as the apparatus to be used to be able to display the captured image for medical use and the related image for medical use together. In addition, as in the third example of the use case, the control of the therapeutic device such as the bipolar can be performed by the medical observation apparatus 100, such that the operation efficiency can be further improved.

[2-4] Example of Effect Achieved by Using Control Method According to Present Embodiment By using the control method according to the present embodiment, the medical observation system according to the present embodiment achieves, for example, the following effects. It goes without saying that the effects achieved by the control method according to the present embodiment are not limited to the following example.

The operator can automatically switch the display of the image output from the medical imaging apparatus used simultaneously with the medical observation apparatus 100 according to the progress of surgery, and further, can control the display pattern by the medical observation apparatus 100 side. In addition, since the operator can easily and quickly set the treatment tool to be used, the instruction to the outside staff such as the outside nurse is output and the time lag up to the operation after the instruction can be reduced. Therefore, the operation efficiency can be improved, the labor of the outside staff can be reduced, which leads to the improvement in the operation efficiency as a whole and furthermore the reduction in the operation cost.

(Program According to Present Embodiment)

A program (for example, a program capable of executing processing related to the control method according to the present embodiment such as "apparatus determination processing and display control processing" or "apparatus determination processing, display control processing, and apparatus control processing") for causing a computer system to function as a medical observation apparatus according to the present embodiment (or a control apparatus according to the present embodiment) is executed by a processor or the like in a computer system to be able to assist a medical worker. Here, examples of the computer system according to the present embodiment include a single computer or a plurality of computers. A series of processing related to the control method according to the present embodiment is performed by the computer system according to the present embodiment.

In addition, the program for causing the computer system to function as the medical observation apparatus according to the present embodiment (or the control apparatus according to the present embodiment) is executed by the processor or the like in the computer system, thereby achieving the effect by the display realized by the processing related to the control method according to the present embodiment as described above.

As described above, the preferred embodiments of the present disclosure have been described in detail with reference to the accompanying drawings, but the technical scope of the present disclosure is not limited to such examples. It will be apparent to those skilled in the art of the present disclosure that various changes or modifications can be conceived within the scope of the technical idea described in the claims, and it is naturally understood that these changes or modifications fall within the technical scope of the present disclosure.

For example, although it has been described that a program (computer program) for causing a computer system to function as a medical observation apparatus according to the present embodiment is provided, the present embodiment can further provide a recording medium storing the above program.

The configuration described above is an example of the present embodiment, and naturally falls within the technical scope of the present disclosure.

In addition, the effects described in the present specification are merely illustrative or exemplary, and are not limited to those described in the present specification. That is, the technology according to the present disclosure can exhibit other effects apparent to those skilled in the art from the description of the present specification, in addition to or instead of the effects described above.

The following configurations are also within the technical scope of the present disclosure.

(1) A medical observation apparatus includes:
a determination unit which determines an apparatus to be used based on a captured image for medical use captured by an imaging device; and
a display control unit which causes a related image for medical use corresponding to the determined apparatus and the captured image for medical use to be displayed.

(2) The medical observation apparatus described in (1), in which the display control unit causes the related image for medical use and the captured image for medical use to be displayed together.

(3) The medical observation apparatus described in (1) or (2), in which the display control unit switches and causes the related image for medical use and the captured image for medical use to be displayed.

(4) The medical observation apparatus described in any one of (1) to (3), in which the determination unit determines an apparatus to be used by detecting an area corresponding to an apparatus to be determined from the captured image for medical use based on apparatus information on the apparatus to be determined to determine use.

(5) The medical observation apparatus described in any one of (1) to (4), in which
when a plurality of apparatuses to be used are determined by the determination unit,
the display control unit causes a related image for medical use corresponding to each of the plurality of determined apparatuses to be displayed.

(6) The medical observation apparatus described in any one of (1) to (5), in which when the determined apparatus is a medical imaging apparatus, the display control unit causes a medical image obtained from the medical imaging apparatus to be displayed as the related image for medical use.

(7) The medical observation apparatus described in any one of (1) to (6), in which the display control unit causes an image indicating setting in the determined apparatus to be displayed as the related image for medical use.

(8) The medical observation apparatus described in any one of (1) to (7) further includes an apparatus control unit which controls the determined apparatus.

(9) The medical observation apparatus described in (8), in which the display control unit causes a related image for medical use corresponding to a control for the determined apparatus to be displayed.

(10) The medical observation apparatus described in any one of (1) to (9), in which the imaging device is supported by an arm configured by connecting a plurality of links to each other with a joint.

(11) The medical observation apparatus described in (10) includes
the arm, and
the imaging device supported by the arm.

(12) A control method executed by a medical observation apparatus, includes:
a step of determining an apparatus to be used based on a captured image for medical use captured by an imaging device; and
a step of displaying a related image for medical use corresponding to the determined apparatus and the captured image for medical use.

REFERENCE SIGNS LIST

100 MEDICAL OBSERVATION APPARATUS
102 BASE
104 ARM
106 IMAGING DEVICE
110a, 110b, 110c, 110d, 110e, 110f JOINT
112a, 112b, 112c, 112d, 112e, 112f LINK
120 IMAGING MEMBER
122 CYLINDRICAL MEMBER
124 ZOOM SWITCH
126 FOCUS SWITCH
128 OPERATION MODE CHANGE SWITCH
152 ARM UNIT
154 IMAGING UNIT
156 COMMUNICATION UNIT
158 STORAGE UNIT
160 CONTROL UNIT
162 IMAGING CONTROL UNIT
164 ARM CONTROL UNIT
166 DISPLAY CONTROL UNIT
168 DETERMINATION UNIT
170 APPARATUS CONTROL UNIT
200 DISPLAY APPARATUS
300 TARGET APPARATUS
1000 MEDICAL OBSERVATION SYSTEM
OP OPERATOR
PA PATIENT
FS FOOT SWITCH

The invention claimed is:

1. A medical observation apparatus comprising:
circuitry configured to
determine an apparatus to be used based on a captured image for medical use captured by an imaging sensor; and
on condition that the determined apparatus is a medical imaging apparatus, cause a related image for medical use output from the determined apparatus and the captured image for medical use to be displayed on a same display.

2. The medical observation apparatus according to claim 1, wherein the circuitry is configured to cause the related image for medical use and the captured image for medical use to be displayed together on the same display.

3. The medical observation apparatus according to claim 1, wherein the circuitry is configured to switch and cause the related image for medical use and the captured image for medical use to be displayed on the same display.

4. The medical observation apparatus according to claim 1, wherein the circuitry is configured to determine an apparatus to be used by detecting an area corresponding to an apparatus to be determined from the captured image for medical use based on apparatus information on the apparatus to be determined to determine use.

5. The medical observation apparatus according to claim 1, wherein the circuitry is configured, on condition that a plurality of apparatuses are determined, to cause a related image for medical use corresponding to each of the plurality of determined apparatuses to be displayed.

6. The medical observation apparatus according to claim 1, wherein the circuitry is configured to cause an image indicating setting in the determined apparatus to be displayed as the related image for medical use.

7. The medical observation apparatus according to claim 1, wherein, on condition that the determined apparatus is a treatment apparatus, the circuitry is configured to control the determined apparatus.

8. The medical observation apparatus according to claim 7, wherein the circuitry is configured to cause a related image for medical use corresponding to a control for the treatment apparatus to be displayed.

9. The medical observation apparatus according to claim 1, wherein the imaging sensor is supported by an arm configured by connecting a plurality of links to each other with a joint.

10. The medical observation apparatus according to claim 9, comprising:
   the arm, and
   the imaging sensor supported by the arm.

11. A control method executed by a medical observation apparatus, the method comprising:
   determining an apparatus to be used based on a captured image for medical use captured by an imaging device; and
   on condition that the determined apparatus is a medical imaging apparatus, displaying a related image for medical use output from the determined apparatus and the captured image for medical use on a same display.

12. The control method according to claim 11, wherein displaying the related image and the captured image on the same display is simultaneous.

13. The control method according to claim 12, wherein displaying the related image and the captured image on the same display together includes overlapping the related image on top of the captured image.

14. The control method according to claim 13, wherein overlapping the related image on top of the captured image includes overlapping the related image in a region of the captured image outside the determined apparatus.

15. The control method according to claim 13, wherein overlapping the related image on top of the captured image includes overlapping the related image having a smaller area than the captured image.

16. The control method according to claim 15, wherein overlapping the related image on top of the captured image includes overlapping the related image at a position in a periphery of the captured image.

17. The medical observation apparatus according to claim 2, wherein displaying the related image and the captured image on the same display includes overlapping the related image on top of the captured image.

18. The medical observation apparatus according to claim 17, wherein overlapping the related image on top of the captured image includes overlapping the related image in a region of the captured image outside the determined apparatus.

19. The medical observation apparatus according to claim 17, wherein overlapping the related image on top of the captured image includes overlapping the related image having a smaller area than the captured image.

20. The medical observation apparatus according to claim 19, wherein overlapping the related image on top of the captured image includes overlapping the related image at a position in a periphery of the captured image.

21. A medical observation apparatus comprising:
   circuitry configured to
      determine an apparatus based on a captured image for medical use captured by an imaging sensor; and
      on condition that the determined apparatus is a medical imaging apparatus, cause a related image for medical use generated based on an output signal from the determined apparatus and the captured image for medical use to be displayed on a same display.

* * * * *